(12) United States Patent
Seo

(10) Patent No.: US 10,889,552 B2
(45) Date of Patent: Jan. 12, 2021

(54) DIHYDROXYBENZAMIDE COMPOUND HAVING HSP90 INHIBITORY ACTIVITY OR PHARMACEUTICALLY ACCEPTABLE SALT THEREOF, AND MEDICAL USE THEREOF

(71) Applicant: ONCOZEN CO., LTD., Seoul (KR)

(72) Inventor: Young Ho Seo, Daegu (KR)

(73) Assignee: ONCOZEN CO.. LTD., Seoul (KR)

( * ) Notice: Subject to any disclaimer, the term of this patent is extended or adjusted under 35 U.S.C. 154(b) by 0 days.

(21) Appl. No.: 16/576,749

(22) Filed: Sep. 19, 2019

(65) Prior Publication Data

US 2020/0010430 A1 Jan. 9, 2020

Related U.S. Application Data

(63) Continuation of application No. 16/073,342, filed as application No. PCT/KR2017/001034 on Jan. 31, 2017, now Pat. No. 10,464,907.

(30) Foreign Application Priority Data

Jan. 29, 2016 (KR) .......................... 10-2016-0011622
Jan. 29, 2016 (KR) .......................... 10-2016-0011626

(51) Int. Cl.
| | | |
|---|---|---|
| C07D 241/04 | (2006.01) | |
| A23L 33/10 | (2016.01) | |
| C07C 237/42 | (2006.01) | |
| C07C 235/60 | (2006.01) | |
| A61P 25/28 | (2006.01) | |
| A61P 31/12 | (2006.01) | |
| A61P 25/16 | (2006.01) | |
| A61P 35/00 | (2006.01) | |

(52) U.S. Cl.
CPC ............ *C07D 241/04* (2013.01); *A23L 33/10* (2016.08); *A61P 25/16* (2018.01); *A61P 25/28* (2018.01); *A61P 31/12* (2018.01); *A61P 35/00* (2018.01); *C07C 235/60* (2013.01); *C07C 237/42* (2013.01)

(58) Field of Classification Search
CPC ........ C07D 241/04; A61P 25/28; A61P 31/12; A61P 25/16; A61P 35/00
USPC ..................................................... 514/255.01
See application file for complete search history.

(56) References Cited

U.S. PATENT DOCUMENTS

| | | | | |
|---|---|---|---|---|
| 2007/0259886 A1* | 11/2007 | Chessari | ............. | C07D 209/44 514/254.09 |
| 2007/0265268 A1 | 11/2007 | Kitamura et al. | | |
| 2008/0306054 A1* | 12/2008 | Chessari | ................ | A61P 37/06 514/227.5 |
| 2009/0215742 A1 | 8/2009 | Funk et al. | | |
| 2010/0311745 A1* | 12/2010 | Eggenweiler | .......... | A61P 25/00 514/235.2 |
| 2013/0143926 A1 | 6/2013 | Graham et al. | | |
| 2015/0045362 A1 | 2/2015 | Chessari et al. | | |

FOREIGN PATENT DOCUMENTS

| | | |
|---|---|---|
| WO | 2006-109075 A2 | 10/2006 |
| WO | 2006-117669 A1 | 11/2006 |
| WO | 2011-154708 A1 | 12/2011 |
| WO | WO-2015040425 A1 * | 3/2015 |
| WO | WO-2018171575 A1 * | 9/2018 |
| WO | 2019-027203 A1 | 2/2019 |

OTHER PUBLICATIONS

Nepali; Bioorganic Chemistry 2019, 91, 103119. (Year: 2019).*
Park; European Journal of Medicinal Chemistry 2018, 143, 390-401. (Year: 2018).*
Solit; Drug Discovery Today 2008, 13, 38-43. (Year: 2008).*
Needham; Journal of Pharmacology and Experimental Therapeutics 2011, 339, 132-142. With supplemental Information, 53 pages. (Year: 2011).*
International Search Report for PCT/KR2017/001034 dated May 15, 2017 from Korean Intellectual Property Office.
Barret, T. N. et al., "Synthesis of C-5-substituted resorcylates and resorcinamides via formylation-aromatization of functionalized keto-dioxinones", Tetrahedron, 2014, vol. 70, No. 38, pp. 6894-6901.
Soo; in vivo 2008, 22, 311-316. (Year: 2008).
Jeong; European Journal of Medicinal Chemistry 2016, 124, 1069-1080. (Year: 2016).
Geller; Biochimica et Biophysica Acta 1823 (2012) 698-706. (Year: 2012).
Wang: Arch Virol 2017, 162, 3269-3282. (Year: 2017).
Lackie; Frontiers in Neuroscience, May 2017, vol. 11, article 254, 23 pages. (Year: 2017).
Luo; Molecular Neuro degeneration 2010, 5, 24, 8 pages. (Year: 2010).

* cited by examiner

*Primary Examiner* — Daniel R Carcanague

(74) *Attorney, Agent, or Firm* — Sughrue Mion, PLLC

(57) ABSTRACT

Disclosed is a novel compound having HSP90 inhibitory activity or a pharmaceutically acceptable salt thereof, and a medicinal use thereof, and composition comprising a dihydroxyphenyl compound or a benzamide compound, which is a novel compound having the HSP90 inhibitory activity of the present invention can effectively inhibit HSP90, and thus can be usefully used as a pharmaceutical composition for preventing or treating HSP90-mediated diseases or a health functional food for preventing or improving HSP90-mediated diseases, which selected from the group consisting of cancer diseases, degenerative neurological diseases and viral infections.

4 Claims, 5 Drawing Sheets

DIHYDROXYBENZAMIDE COMPOUND HAVING HSP90 INHIBITORY ACTIVITY OR PHARMACEUTICALLY ACCEPTABLE SALT THEREOF, AND MEDICAL USE THEREOF

CROSS REFERENCE TO PRIOR APPLICATIONS

This application is a Continuation Application of U.S. patent application Ser. No. 16/073,342 filed on Jul. 27, 2018 under 35 U.S.C. § 120, which is the 35 U.S.C. 371 national stage of International application PCT/KR2017/001034 filed on Jan. 31, 2017, which claims priority to Korean applications 10-2016-0011626 filed on Jan. 29, 2016 and 10-2016-0011622 filed on Jan. 29, 2016, the entire contents of each of the above-identified applications are hereby incorporated by reference.

BACKGROUND

The present invention relates to a novel compound having HSP90 inhibitory activity or a pharmaceutically acceptable salt thereof and a medical use thereof.

A HSP90 protein is one of the most abundant chaperones within eukaryotic cells and is responsible for stabilization and activity regulation of various proteins related to cell growth differentiation and survival. The substrate protein of the HSP90 which is called the client protein contains over 50 cancer-inducing proteins. If the HSP90 activity is inhibited, the HSP90 client proteins are degraded by the proteasome.

Therefore, the HSP90 activity inhibitor can decrease the activity of various cancer-inducing proteins at the same time and thus it has attracted great attention as an anticancer agent capable of being applied to a wide variety of cancers. In particular, HSP90 has been reported to be effective treatment of cancer with resistance, because it simultaneously reduces activity of various cancer-inducing proteins.

In addition, it has been reported that HSP90 inhibitor may be used as a therapeutic agent for degenerative neurological diseases, because proteins that cause degenerative nerve diseases are also present in the HSP90 client proteins.

The HSP90 inhibitor started with the development of the natural substance geldanamycin (GA). GA has been found to lead to the decomposition of Src, the client protein via inhibition of HSP90 in 1994 and thereafter inhibitors of targeting HSP90 have been developed actively. However, GA has a strong anticancer effect, but has problems of liver toxicity, solubility and stability. To compensate it. GA derivatives such as Tanespimycin (17-AAG), alvespimycin (17-DMAG) and retaspimycin are developed, but the problem has not been solved by the structural characteristics of GA. HSP90 inhibitors of various structures have been researched at the clinical stage, but since FDA-approved drug has not yet been developed, new and strong efficacious compounds are required.

Accordingly, an object of the present invention is to provide a novel dihydroxyphenyl compound or a benzamide compound.

Also, another object of the present invention is to provide a pharmaceutical composition for preventing or treating HSP90-mediated diseases comprising a novel dihydroxyphenyl compound or benzamide compound, as an active ingredient.

In addition, another object of the present invention is to provide a health functional food for preventing or improving HSP90-mediated disease comprising a novel dihydroxyphenyl compound or benzamide compound, as an active ingredient.

SUMMARY

In order to achieve the above object, the present invention provides a dihydroxyphenyl-based compound represented by following Chemical Formula 1, a stereoisomer thereof, a racemic mixture thereof or a pharmaceutically acceptable salt thereof:

[Chemical Formula 1]

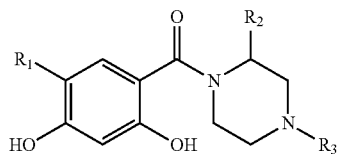

in Chemical Formula 1,
$R_1$ is any one selected from the group consisting of halogen, C1-C4 alkyl and C1-C4 alkoxy,
$R_2$ is any one selected from the group consisting of C3-C6 cycloalkyl, phenyl, halogen, C1-C4 alkyl and C1-C4 alkoxy, and
$R_3$ is C1-C4 alkyl or C1-C4 alkoxy.

Also, the present invention provides a pharmaceutical composition for preventing or treating heat shock protein 90 (HSP90)-mediated disease comprising a dihydroxyphenyl-based compound represented by the above Chemical Formula 1, a stereoisomer thereof, a racemic mixture thereof or a pharmaceutically acceptable salt thereof, as an active ingredient.

In addition, the present invention provides a health functional food for preventing or improving heat shock protein 90 (ISP90)-mediated disease comprising a dihydroxyphenyl-based compound represented by the above Chemical Formula 1, a stereoisomer thereof, a racemic mixture thereof or a pharmaceutically acceptable salt thereof, as an active ingredient.

Further, the present invention provides a benzamide compound represented by following Chemical Formula 2 or a pharmaceutically acceptable salt thereof:

[Chemical Formula 2]

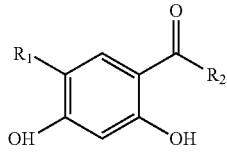

In Chemical Formula 2,
$R_1$ is halogen or C1-C4 alkyl,
$R_2$ is

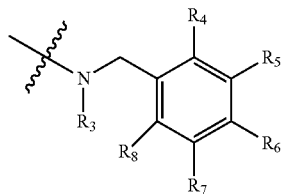

or

-continued each of $R_3$ and $R_4$ can be the same as or different from to each other and is any one selected from the group consisting of H, C1-C4 alkyl and C1-C4 alkoxy, each of $R_5$ and $R_6$ can be the same as or different from to each other and is any one selected from the group consisting of H, C1-C4 alkyl and C1-C4 alkoxy, or $R_5$ and $R_6$ are connected to each other to form 5- or 6-membered ring, $R_7$ is any one selected from the group consisting of H, C1-C4 alkyl and C1-C4 alkoxy, $R_8$ is H or halogen, R9 is any one selected from the group consisting of C1-C4 alkyl, C1-C4 alkoxy and benzyl groups.

Also, the present invention provides a pharmaceutical composition for preventing or treating heat shock protein 90 (HSP90)-mediated disease comprising a benzamide compound represented by the above Chemical Formula 2 or a pharmaceutically acceptable salt thereof, as an active ingredient.

In addition, the present invention provides a health functional food for preventing or improving heat shock protein 90 (HSP90)-mediated disease comprising a benzamide compound represented by the above Chemical Formula 2 or a pharmaceutically acceptable salt thereof, as an active ingredient.

A composition comprising a dihydroxyphenyl compound or a benzamide compound, which is a novel compound having the HSP90 inhibitory activity according to the present invention, can effectively inhibit HSP90, and thus is useful as a pharmaceutical composition for preventing or treating HSP90-mediated disease or a health functional food for preventing or improving HSP90-mediated disease, which is selected from the group consisting of a cancer disease, a degenerative neurological disease and a viral infection.

DETAILED DESCRIPTION

Figure 1:
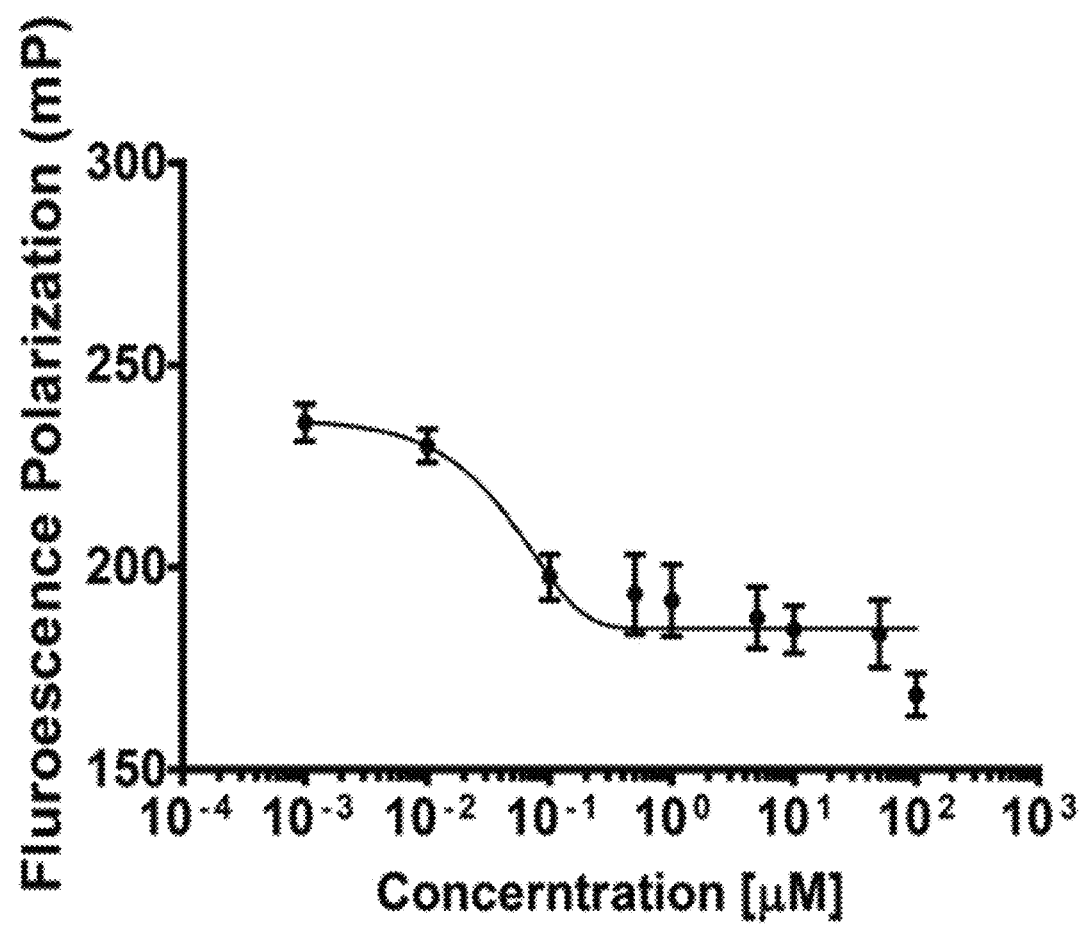
FIG. 1 shows the results of confirming HSP90 inhibitory activity by Compound 17 according to Example 1 of the present invention.

Hereinafter, the present invention will be described in detail.

The inventors of the present invention have studied a compound showing heat shock protein 90 (HSP90) inhibitory effect and synthesized a compound represented by the following formula 1 and completed the present invention by confirming its HSP90 inhibitory effect.

Accordingly, the present invention provides a dihydroxyphenyl-based compound represented by following Chemical Formula 1, a stereoisomer thereof, a racemic mixture thereof or a pharmaceutically acceptable salt thereof:

[Chemical Formula 1]

wherein $R_1$ is any one selected from the group consisting of halogen, C1-C4 alkyl and C1-C4 alkoxy, $R_2$ is any one selected from the group consisting of C3-C6 cycloalkyl, phenyl, halogen, C1-C4 alkyl and C1-C4 alkoxy, and $R_3$ is C1-C4 alkyl or C1-C4 alkoxy.

In the dihydroxyphenyl-based compound represented by the Chemical Formula 1, $R_1$ is C1-C4 alkyl, $R_2$ is phenyl and $R_3$ is C1-C4 alkyl.

The present invention also relates to a pharmaceutical composition for preventing or treating heat shock protein 90 (HSP90)-mediated disease comprising a dihydroxyphenyl-based compound represented by following Chemical Formula 1, a stereoisomer thereof, a racemic mixture thereof or a pharmaceutically acceptable salt thereof, as an active ingredient:

[Chemical Formula 1]

wherein $R_1$ is any one selected from the group consisting of halogen, C1-C4 alkyl and C1-C4 alkoxy, $R_2$ is any one selected from the group consisting of C3-C6 cycloalkyl, phenyl, halogen, C1-C4 alkyl and C1-C4 alkoxy, and $R_3$ is C1-C4 alkyl or C1-C4 alkoxy.

In the dihydroxyphenyl-based compound represented by the Chemical Formula 1, $R_1$ is C1-C4 alkyl, $R_2$ is phenyl and $R_3$ is C1-C4 alkyl.

The heat shock protein 90-mediated disease is one or more diseases selected from the group consisting of cancer diseases, degenerative neurological diseases and viral infections.

The cancer can be selected from the group consisting of non-small cell lung cancer, breast cancer, ovarian cancer, uterine cancer, pancreatic cancer, lung cancer, gastric cancer, liver cancer, colon cancer, skin cancer, head or neck cancer, brain cancer, larynaeal cancer, prostate cancer, bladder cancer, esophageal cancer, thyroid cancer, kidney cancer, rectal cancer, acute alyelogenous leukemia, chronic myelogenous leukemia, acute lymphoblastic leukemia, chronic lymphocytic leukemia and blood cancer, but is not limited thereto.

The degenerative neurological disease is selected from the group consisting of stroke, paralysis, memory loss, memory impairment, dementia, forgetfulness, Parkinson's disease, Alzheimer's disease, Pick's disease, Creutzfeld-Kacob disease, Huntington's disease and amyotrophic lateral sclerosis, but is not limited thereto.

Also, the present invention also relates to a health functional food for preventing or improving heat shock protein 90 (HSP90)-mediated disease comprising a dihydroxyphenyl-based compound represented by following Chemical Formula 1, a stereoisomer thereof, a racemic mixture thereof or a pharmaceutically acceptable salt thereof, as an active ingredient:

[Chemical Formula 1]

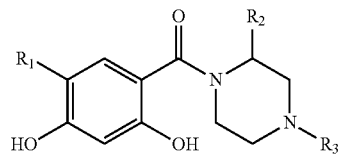

wherein $R_1$ is any one selected from the group consisting of halogen, C1-C4 alkyl and C1-C4 alkoxy, $R_2$ is any one selected from the group consisting of C3-C6 cycloalkyl, phenyl, halogen, C1-C4 alkyl and C1-C4 alkoxy, and $R_3$ is C1-C4 alkyl or C1-C4 alkoxy.

Also, the inventors of the present invention also studied a compound showing Heat Shock Protein 90 (HSP90) inhibitory effect, and synthesized a compound represented by the following Chemical Formula 2 and confirmed its HSP90 inhibitory effect to complete the present invention.

Accordingly, the present invention provides a benzamide compound represented by following Chemical Formula 2 or a pharmaceutically acceptable salt thereof:

[Chemical Formula 2]

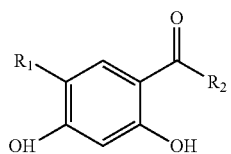

wherein $R_1$ is halogen or C1-C4 alkyl,
$R_2$ is

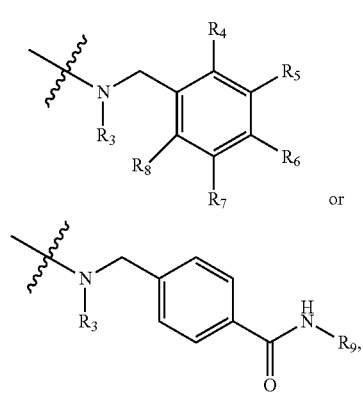

or each of $R_3$ and $R_4$ can be the same as or different from to each other and is any one selected from the group consisting of H, C1-C4 alkyl and C1-C4 alkoxy, each of $R_5$ and $R_6$ can be the same as or different from to each other and is any one selected from the group consisting of H, C1-C4 alkyl and C1-C4 alkoxy, or $R_5$ and $R_6$ are connected to each other to form 5- or 6-membered ring.

$R_7$ is any one selected from the group consisting of H, C1-C4 alkyl and C1-C4 alkoxy.

$R_8$ is H or halogen, $R_9$ is any one selected from the group consisting of C1-C4 alkyl, C1-C4 alkoxy and benzyl groups.

In the benzamide compound represented by the Chemical Formula 2, $R_1$ is halogen or C1-C4 alkyl, and $R_2$ is

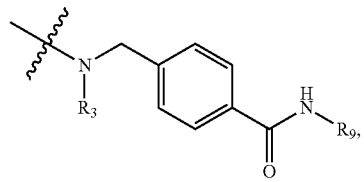

$R_3$ is any one selected from the group consisting of H, C1-C4 alkyl and C1-C4 alkoxy, and $R_9$ is any one selected from the group consisting of C1-C4 alkyl, C1-C4 alkoxy and benzyl groups.

The benzamide compound represented by the Chemical Formula 2 can be any one selected from the group consisting of N-benzyl-5-chloro-2,4-dihydroxybenzamide, N-benzyl-5-chloro-2,4-dihydroxy-N-methylbenzamide, 5-chloro-2,4-dihydroxy-N-(4-methoxy benzyl)-N-methylbenzamide, 5-chloro-N-(3,4-dimethoxybenzyl)-2,4-dihydroxy-N-methylbenzamide, N-(benzo[d][1,3]dioxol-5-ylmethyl)-5-chloro-2,4-dihydroxy-N-methylbenzamide, 5-chloro-2,4-dihydroxy-N-methyl-N-(3,4,5-trimethoxybenzyl)benzamide, 5-chloro-N-(2-chloro-3,4,5-trimethoxybenzyl)-2,4-dihydroxy-N-methylbenzamide, N-(2-bromo-3,4,5-trimethoxybenzyl)-5-chloro-2,4-dihydroxy-N-methylbenzamide, 5-chloro-2,4-dihydroxy-N-methyl-N-(3-methylbenzyl)benzamide, 5-chloro-2,4-dihydroxy-N-methyl-N-(2-methylbenzyl)benzamide, 5-chloro-2,4-dihydroxy-N-methyl-N-(4-methylbenzyl)benzamide, 5-chloro-2,4-dihydroxy-N-methyl-N-(4-(methylcarbamoyl)benzyl)benzamide, 5-chloro-N-(4-(ethylcarbamoyl)benzyl)-2,4-dihydroxy-N-methylbenzamide, 5-chloro-2,4-dihydroxy-N-methyl-N-(4-(propylcarbamoyl)benzyl)benzamide, 2,4-dihydroxy-5-isopropyl-N-methyl-N-(4-(methylcarbamoyl)benzyl) benzamide, N-(4-(ethylcarbamoyl)benzyl)-2,4-dihydroxy-5-isopropyl-N-methylbenzamide, 2,4-dihydroxy-5-isopropyl-N-methyl-N-(4-(propylcarbamoyl)benzyl) benzamide and N-benzyl-2,4-dihydroxy-5-isopropyl-N-methylbenzamide and preferably 2,4-dihydroxy-5-isopropyl-N-methyl-N-(4-(propylcarbamoyl)benzyl) benzamide.

In addition, the present invention also provides a pharmaceutical composition for preventing or treating heat shock protein 90 (HSP90)-mediated disease comprising a benzamide compound represented by following Chemical Formula 2 or a pharmaceutically acceptable salt thereof, as an active ingredient:

[Chemical Formula 2]

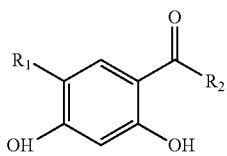

wherein $R_1$ is halogen or C1-C4 alkyl,
$R_2$ is

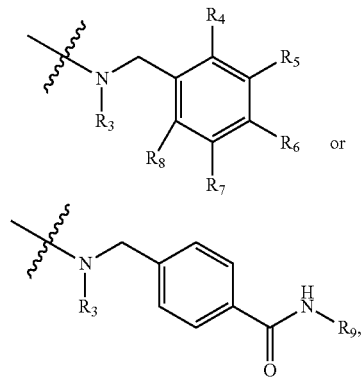

each of $R_3$ and $R_4$ can be the same as or different from to each other and is any one selected from the group consisting of H, C1-C4 alkyl and C1-C4 alkoxy,
each of $R_5$ and $R_6$ can be the same as or different from to each other and is any one selected from the group consisting of H, C1-C4 alkyl and C1-C4 alkoxy, or $R_5$ and $R_6$ are connected to each other to form 5- or 6-membered ring,
$R_7$ is any one selected from the group consisting of H, C1-C4 alkyl and C1-C4 alkoxy,
$R_8$ is H or halogen,
$R_9$ is any one selected from the group consisting of C1-C4 alkyl, C1-C4 alkoxy and benzyl groups.

In the benzamide compound represented by the Chemical Formula 2, $R_1$ can be halogen or C1-C4 alkyl, and $R_2$ is

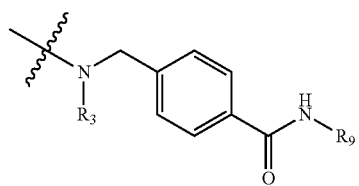

$R_3$ can be any one selected from the group consisting of H, C1-C4 alkyl and C1-C4 alkoxy, and $R_9$ can be any one selected from the group consisting of C1-C4 alkyl, C1-C4 alkoxy and benzyl groups.

The benzamide compound represented by the Chemical Formula 2 can be any one selected from the group consisting of N-benzyl-5-chloro-2,4-dihydroxybenzamide, N-benzyl-5-chloro-2,4-dihydroxy-N-methylbenzamide, 5-chloro-2,4-dihydroxy-N-(4-methoxybenzyl)-N-methylbenzamide, 5-chloro-N-(3,4-dimethoxybenzyl)-2,4-dihydroxy-N-methylbenzamide, N-(benzo[d][1,3]dioxol-5-ylmethyl)-5-chloro-2,4-dihydroxy-N-methylbenzamide, 5-chloro-2,4-dihydroxy-N-methyl-N-(3,4,5-trimethoxybenzyl)benzamide, 5-chloro-N-(2-chloro-3,4,5-trimethoxybenzyl)-2,4-dihydroxy-N-methylbenzamide, N-(2-bromo-3,4,5-trimethoxybenzyl)-5-chloro-2,4-dihydroxy-N-methylbenzamide, 5-chloro-2,4-dihydroxy-N-methyl-N-(3-methylbenzyl)benzamide, 5-chloro-2,4-dihydroxy-N-methyl-N-(2-methylbenzyl)benzamide, 5-chloro-2,4-dihydroxy-N-methyl-N-(4-methylbenzyl)benzamide, 5-chloro-2,4-dihydroxy-N-methyl-N-(4-(methylcarbamoyl)benzyl)benzamide, 5-chloro-N-(4-(ethylcarbamoyl)benzyl)-2,4-dihydroxy-N-methylbenzamide, 5-chloro-2,4-dihydroxy-N-methyl-N-(4-(propylcarbamoyl)benzyl)benzamide, 2,4-dihydroxy-5-isopropyl-N-methyl-N-(4-(methylcarbamoyl)benzyl)benzamide, N-(4-(ethylcarbamoyl)benzyl)-2,4-dihydroxy-5-isopropyl-N-methylbenzamide, 2,4-dihydroxy-5-isopropyl-N-methyl-N-(4-(propylcarbamoyl)benzyl)benzamide and N-benzyl-2,4-dihydroxy-5-isopropyl-N-methylbenzamide and preferably 2,4-dihydroxy-5-isopropyl-N-methyl-N-(4-(propylcarbamoyl)benzyl)benzamide.

The heat shock protein 90 mediated disease is at least one selected from the group consisting of cancer diseases, degenerative neurological diseases and viral infections.

The cancer disease can be any one selected from the group consisting of non-small cell lung cancer, breast cancer, ovarian cancer, uterine cancer, pancreatic cancer, lung cancer, gastric cancer, liver cancer, colon cancer, skin cancer, head or neck cancer, brain cancer, laryngeal cancer, prostate cancer, bladder cancer, esophageal cancer, thyroid cancer, kidney cancer, rectal cancer, acute myelogenous leukemia, chronic myelogenous leukemia, acute lymphoblastic leukemia, chronic lymphocytic leukemia, and blood cancer, but is not limited thereto.

The degenerative neurological disease can be any one selected from the group consisting of stroke, paralysis, memory loss, memory impairment, dementia, forgetfulness, Parkinson's disease, Alzheimer's disease, Pick's disease, Creutzfeld-Kacob disease, Huntington's disease and amyotrophic lateral sclerosis, but is not limited thereto.

Furthermore, the present invention provides a health functional food for preventing or improving heat shock protein 90 (HSP90)-mediated disease comprising a benzamide compound represented by following Chemical Formula 2 or a pharmaceutically acceptable salt thereof, as an active ingredient:

[Chemical Formula 2]

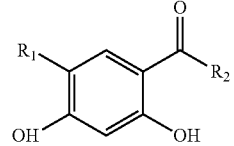

wherein $R_1$ is halogen or C1-C4 alkyl,
$R_2$ is

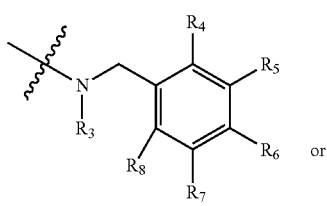

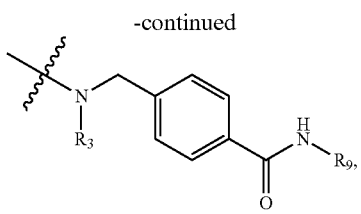

each of $R_3$ and $R_4$ can be the same as or different from to each other and is any one selected from the group consisting of H, C1-C4 alkyl and C1-C4 alkoxy, each of $R_5$ and $R_6$ can be the same as or different from to each other and is any one selected from the group consisting of H, C1-C4 alkyl and C1-C4 alkoxy, or $R_5$ and $R_6$ are connected to each other to form 5- or 6-membered ring, $R_7$ is any one selected from the group consisting of H, C1-C4 alkyl and C1-C4 alkoxy, $R_8$ is H or halogen, $R_9$ is any one selected from the group consisting of C1-C4 alkyl C1-C4 alkoxy and benzyl groups.

In the benzamide compound represented by the Chemical Formula 2, $R_1$ can be halogen or C1-C4 alkyl, and $R_2$ can be

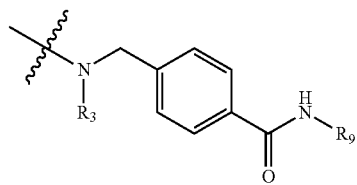

$R_3$ can be any one selected from the group consisting of H, C1-C4 alkyl and C1-C4 alkoxy, and $R_9$ is any one selected from the group consisting of C1-C4 alkyl, C1-C4 alkoxy and benzyl groups.

The benzamide compound represented by the Chemical Formula 2 can be any one selected from the group consisting of N-benzyl-5-chloro-2,4-dihydroxybenzamide, N-benzyl-5-chloro-2,4-dihydroxy-N-methylbenzamide, 5-chloro-2,4-dihydroxy-N-(4-methoxybenzyl)-N-methylbenzamide, 5-chloro-N-(3,4-dimethoxybenzyl)-2,4-dihydroxy-N-methylbenzamide, N-(benzo[d][1,3]dioxol-5-ylmethyl)-5-chloro-2,4-dihydroxy-N-methylbenzamide, 5-chloro-2,4-dihydroxy-N-methyl-N-(3,4,5-trimethoxybenzyl)benzamide, 5-chloro-N-(2-chloro-3,4,5-trimethoxybenzyl)-2,4-dihydroxy-N-methylbenzamide, N-(2-bromo-3,4,5-trimethoxybenzyl)-5-chloro-2,4-dihydroxy-N-methylbenzamide, 5-chloro-2,4-dihydroxy-N-methyl-N-(3-methylbenzyl)benzamide, 5-chloro-2,4-dihydroxy-N-methyl-N-(2-methylbenzyl)benzamide, 5-chloro-2,4-dihydroxy-N-methyl-N-(4-methylbenzyl)benzamide, 5-chloro-2,4-dihydroxy-N-methyl-N-(4-(methylcarbamoyl)benzyl)benzamide, 5-chloro-N-(4-(ethylcarbamoyl)benzyl)-2,4-dihydroxy-N-methylbenzamide, 5-chloro-2,4-dihydroxy-N-methyl-N-(4-(propylcarbamoyl)benzyl)benzamide, 2,4-dihydroxy-5-isopropyl-N-methyl-N-(4-(methylcarbamoyl)benzyl)benzamide, N-(4-(ethylcarbamoyl)benzyl)-2,4-dihydroxy-5-isopropyl-N-methylbenzamide, 2,4-dihydroxy-5-isopropyl-N-methyl-N-(4-(propylcarbamoyl)benzyl)benzamide and N-benzyl-2,4-dihydroxy-5-isopropyl-N-methylbenzamide, and preferably 2,4-dihydroxy-5-isopropyl-N-methyl-N-(4-(propylcarbamoyl)benzyl)benzamide.

The pharmaceutical compositions according to the present invention may further comprise suitable carriers, excipients or diluents conventionally used in the manufacture of pharmaceutical compositions.

Examples of carriers, excipients or diluents which can be used in the present invention include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methythydroxybenzoate, propylhydroxybenzoate, talc, magnesium stearate or mineral oil, etc.

The pharmaceutical composition according to the present invention may be formulated as oral preparations such as powders, granules, tablets, capsules, suspensions, emulsions, syrups, aerosols or the like, externals, suppositories and sterilized injection solutions according to a conventional method.

In the case of formulation, a diluent or excipient such as commonly used filler, an extender, a binder, a wetting agent, a disintegrant, a surfactant or the like is used. Solid formulations for oral administration include tablets, pills, powders, granules, capsules, etc., which may contain at least one excipient such as starch, calcium carbonate, sucrose, lactose, gelatin, and the like.

In addition to simple excipients, lubricants such as magnesium stearate and talc are also used. Examples of the liquid preparation for oral administration include suspensions, internal solutions, emulsions, syrups and the like and various excipients such as wetting agents, sweeteners, fragrances and preservatives may be included in addition to water and liquid paraffin which are commonly used simple diluents.

Formulations for parenteral administration include sterile aqueous solutions, non-aqueous solutions, suspensions, emulsions, freeze-dried preparations, and suppositories. Examples of the non-aqueous solutions or suspending agent include propylene glycol, polyethylene glycol, vegetable oil such as olive oil, injectable ester such as ethyl oleate, and the like. Witepsol, macrogol, tween 61, cacao paper, laurin, glycerogelatin and the like can be used, as the base of suppositories.

Further, the dosage of the pharmaceutical composition according to the present invention may be increased or decreased depending on the route of administration, degree of disease, sex, weight, age, and the like. Accordingly, the dosage amounts do not in any way limit the scope of the invention.

The pharmaceutical composition may be administered to mammals such as rats, mice, livestock, humans, and the like in a various routes. All modes of administration may be expected, for example, by oral, rectal or intravenous, intramuscular, subcutaneous, intratracheal, intrauterine, or intracerebroventricular injections.

The dihydroxyphenyl-based compound or the benzamide compound of the present invention can be used in the form of a pharmaceutically acceptable salt and an acid addition salt formed by a pharmaceutically acceptable free acid is useful as the salt. As the free acid, inorganic acid and organic acid can be used. As the inorganic acid, hydrochloric acid, bromic acid, sulfuric acid, sulfurous acid, phosphoric acid, etc. can be used and as the organic acid, citric acid, acetic acid, maleic acid, fumaric acid, glycolic acid, methanesulfonic acid, acetic acid, glycolic acid, succinic acid, tartaric acid, 4-toluenesulfonic acid, galacturonic acid, embonic acid, glutamic acid, citric acid and aspartic acid. Preferably, hydrochloric acid is used as the inorganic acid, and methanesulfonic acid is used as the organic acid.

In addition, the dihydroxyphenyl-based compound or benzamide compound of the present invention includes not only pharmaceutically acceptable salts, but also all salts, hydrates and solvates which can be prepared by a conventional method.

The addition salt according to the present invention can be prepared by a conventional method and for example, by dissolving the dihydroxyphenyl-based compound of Chemical Formula 1 in a water-miscible organic solvent such as acetone, methanol, ethanol, acetonitrile or the like and adding an organic acid or by adding an aqueous acid solution of an inorganic acid, followed by precipitation or crystallization. Subsequently, a solvent or an excess acid may be evaporated from the mixture and then dried to obtain an additional salt or the precipitated salt may be suction filtrated.

The health functional food according to the present invention may be provided in the form of powder, granule, tablet, capsule, syrup or beverage. Other food or food additives can be used together in addition to the health functional food may be a compound represented by the above Chemical Formula 1 or 2 and can be suitably used according to a conventional method. The amount of the active ingredient to be mixed can be appropriately determined according to its use purpose, for example, prevention, health or therapeutic treatment.

The compound represented by Chemical Formula 1 or 2 contained in the health functional food may be used in accordance with the effective dose of the pharmaceutical composition but may be used for health and hygiene purposes or for a long period. It may be less than the above range, and since the active ingredient has no problem in terms of safety, it can be used in an amount exceeding the above range.

There is no particular limitation on the kind of the health functional food. Examples of the health functional food include meat, sausage, bread, chocolate, candy, snack, confectionery, pizza, ramen, other noodles, gums, dairy products including ice cream, soup, beverage, tea, drinks, an alcoholic beverage, and a vitamin complex.

Hereinafter, the present invention will be described in detail with reference to the following examples. It should be noted, however, that the following examples are illustrative of the present invention and are not intended to limit the scope of the present invention. Embodiments of the present invention are provided to more fully describe the present invention to those skilled in the art.

I. Synthesis of Dihydroxyphenyl Compounds and Evaluation of Biological Activity

REFERENCE EXAMPLE 1

1. Reagents and Laboratory Equipment

All reagents and solvents were purchased from the manufacturer and used without further purification.

All experiments dealing with moisture sensitive compounds were performed under an argon atmosphere.

Concentration or solvent removal was carried out using a rotary evaporator under reduced pressure.

Analytical thin layer chromatography was performed on precoated silica gel F254 TLC plates (silica gel F254 TLC plates, E, Merck) and UV light was visualized by staining with iodine gas.

Column chromatography can be performed on medium pressure on silica (Merck Silica gel 40-63 μm) or in Biotage SP1 flash purification system (Biotage SP1) using prepacked silica gel cartridges (Biotage).

NMR analysis was carried out using ARX-300 (300 MHz or more) manufactured by Bruker.

Chemical shifts were recorded in per million (δ). The deuterium lock signal of the sample solvent was used as a reference, and the coupling constants (J) were recorded in hertz (Hz).

The splitting pattern abbreviations are: s, singlet; d, doublet; t, triplet; q, quartet, dd, doublet of doublets; m, multiplet.

2. Cell Culture

Sk-Br3 (Korean cell line bank), a breast cancer cell, and H1975 cell (ATCC), a nonsmall cell lung cancer, were cultured in RPMI 1640 containing 25 mM HEPES (4-(2-hydroxyethyl)-1-piperazineethanesulfonic acid) and RPMI 1640 containing L-glutamine (containing streptomycin (500 mg/mL), penicillin (100 units/mL) and 10% fetal bovine serum (FBS)).

The cells were cultured under a humidified atmosphere of 37° C. and 5% $CO_2$.

EXAMPLE 1

Synthesis of Dihydroxyphenyl Compound

Compounds 5 to 9, Compounds 10a to 10i and Compounds 11a to 11j were synthesized in the manner as Reaction Scheme 1 below.

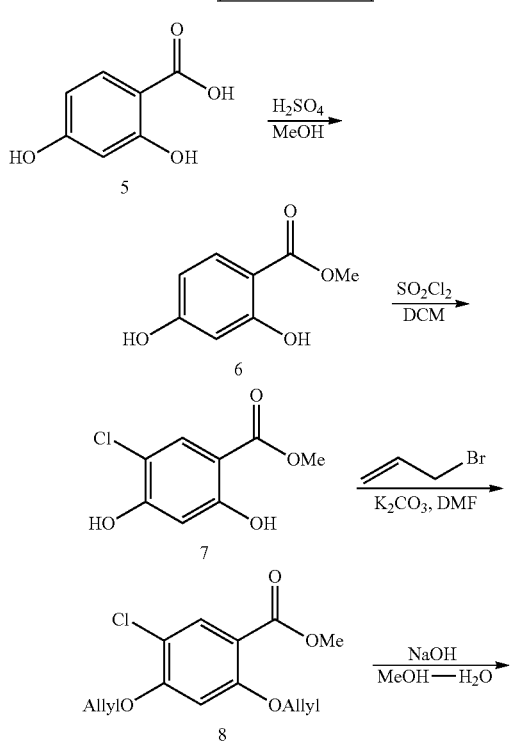

Compound 11a, 11d and 11g to 11i were obtained using the above-synthesized carboxylic acid ester 7.

The carboxylic acid ester 7 was converted to carboxylic acid 18 using sodium hydroxide in methanol without aryl-protection.

2,4-dihydroxybenzoic acid (5) was treated with sulfuric acid in methanol to obtain 2,4-dihydroxybenzoate (6) at a yield of 99%.

The chlorination of 2,4-dihydroxybenzoate (6) and sulfuryl chloride leads to the formation of chlorinated product (7) and its region-isomer, methyl 3-chloro-2,4-dihydroxybenzoate in a molar ratio of 10:1. The formed region-isomer was removed by silica gel chromatography carefully.

Compound 7 was protected with an allyl bromide in the presence of potassium carbonate to obtain an allyl-protected ester 8 in a yield of 99%.

Thereafter, the ester 8 was converted to the carboxylic acid 9 in a yield of 97% using water and sodium hydroxide in methanol.

In addition, the amide coupling reaction between the carboxylic acid 9 and various amines is carried out in the presence of diisopropylethylamine (DIPEA) in ethylene dichloride (EDC), hydroxybenzotriazole (HOBt) or dimethylformamide (DMF) to obtain amides 10a to 10j.

Finally, the aryl-protected group was removed using $PdCl_2(PPh_3)_2$ and ammonium formate under microwave irradiation to obtain Compounds 11a to 11j.

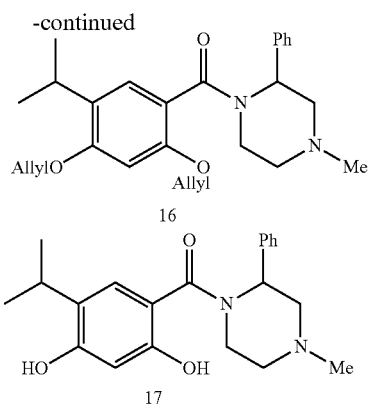

The Friedel-Crafts alkylation of methyl 2,4-dihydroxybenzoate (6) was carried out together with isopropyl bromide and aluminum chloride.

Compound 12 was protected with aryl bromide in the presence of potassium carbonate to produce ester 13, which was converted using sodium hydroxide to obtain carboxylic acid 14 in a yield 58%.

The amide coupling reaction of the carboxylic acid 14 with 1-methyl-3-phenylpiperazine (15) was carried out in the presence of DIPEA in EDC, HOBt or DMF to obtain an amide 16.

Finally, the aryl-protected group was removed using PdCl$_2$(PPh$_3$)$_2$ and ammonium formate under microwave irradiation to obtain Compound 17.

1. Methyl 2,4-dihydroxybenzoate (6)

2,4-dihydroxybenzoic acid (10.2 g, 66.0 mmol) and sulfuric acid (5 mL) in methanol (MeOH, 40 mL) were stirred under argon with refluxing condenser at 100° C. for 12 hours. The mixture was cooled to room temperature, concentrated under pressure and poured into 40 mL of H$_2$O in an ice bath.

The resulting white solid was dissolved in ethyl acetate and then washed with saturated NaHCO$_3$ solution to filter it. The organic layer was dried over Na$_2$SO$_4$ and pressure seas applied to produce Compound 6 in a yield of 86%.

R$_f$=0.20 (2:8 ethyl acetate:hexane). $^1$H NMR (400 MHz, CDCl$_3$) δ 10.97 (s, 1H), 7.74 (d, J=8.8 Hz, 1H), 6.40 (d, J=2.0 Hz, 1H), 6.37 (dd, J=8.8 Hz, 2.4 Hz, 1H), 5.36 (s, 1H), 3.91 (s, 1H).

2. Methyl-5-chloro-2,4-dihydroxybenzoate (7)

Compound 6 (10.0 g, 59.5 mmol) and sulfonyl chloride (4.30 mL, 59.5 mmol) in methylene chloride (CH$_2$Cl$_2$) were stirred at 0° C. for 24 hours under argon.

The mixture was neutralized with 10% NaOH to pH 5, concentrated under pressure and then extracted with ethyl acetate.

The organic layer was washed three times with saturated NaHCO$_3$ solution, dried over Na$_2$SO$_4$ and concentrated under pressure to obtain Compound 7 in a yield of 45%.

R$_f$=0.26 (2:8 ethyl acetate:hexane). $^1$H NMR (400 MHz, CDCl$_3$) δ 10.84 (s, 1H), 7.81 (s, 1H), 6.61 (s, 1H), 6.00 (s, 1H), 3.92 (s, 3H). $^{13}$C NMR (100 MHz, CDCl$_3$) δ 169.6, 162.5, 157.3, 130.3, 111.5, 106.8, 104.3, 52.6

3. Methyl 2,4-bis(allyloxy)-5-chlorobenzoate (8)

A mixture of Compound 7 (6.09 g, 30.00 mmol), acyl bromide (6.75 ml, 78.02 mmol) and potassium carbonate (10.78 mL, 78.02 mmol) in DMF was stirred under argon at room temperature for 24 hours. The mixture was concentrated under pressure and extracted with ethyl acetate.

The organic layer was washed three times with saturated NaHCO$_3$ solution, dried over Na$_2$SO$_4$ and concentrated under pressure to obtain Compound 8 in a yield of 100%.

R$_f$=0.30 (2:8 ethyl acetate:hexane). $^1$H NMR (400 MHz, CDCl$_3$) δ 7.80 (s, 1H), 6.39 (s, 1H), 5.99-5.91 (m, 2H), 5.45 (dd, J=17.2 Hz, 1.2 Hz, 1H), 5.39 (dd, J=17.2 Hz, 0.8 Hz, 1H), 5.25 (d, J=8.0 Hz, 1H), 5.23 (d, J=8.4 Hz, 1H), 4.51 (dd, J=14.8 Hz, 5.2 Hz, 4H), 3.77 (s, 3H). $^{13}$C NMR (100 MHz, CDCl$_3$) δ 164.7, 158.7, 157.7, 133.0, 132.2, 131.7, 118.1, 117.4, 113.9, 112.6, 99.4, 69.7, 51.6

4. 2,4-bis(allyloxy)-5-chlorobenzoic Acid (9)

Compound 8 (9.43 g. 37.99 mmol) and 25 ml of methanol-25 ml of sodium hydroxide in H$_2$O (5 g, 10%) were stirred at room temperature for 30 hours. The mixture was neutralized with 1N HCl to pH 6 and extracted three times with ethyl acetate.

The organic layer was dried over Na$_2$SO$_4$ and concentrated under pressure to obtain Compound 9 in a yield of 80%.

R$_f$=0.11 (4:6 ethyl acetate:hexane). $^1$H NMR (400 MHz, CDCl$_3$) δ 8.16(s, 1H), 6.54(s, 1H), 6.10-5.99(m, 2H), 5.51-5.35(m, 2H), 4.76-4.65(m, 4H).

5. (2,4-bis(allyloxy)-5-chlorophenyl)(pyrrolidin-1-yl)methanone (10a)

Compound 9 (0.36 g. 11.33 mmol), pyrrolidine (0.13 ml, 1.60 mmol), N,N'-dicyclohexylcarbodiimide (0.41 g, 2.00 mmol), 1-hydroxybenzotriazole (0.22 g, 1.60 mmol) and N,N-diisopropylethylamine (0.23 mL, 1.33 mmol) were dissolved in 4 ml of DMF and stirred at 120° C. for 3 hours under microwave irradiation (using Biotage Initiator).

The mixture was dissolved in ethyl acetate and the organic layer was washed with water, dried over Na$_2$SO$_4$ and concentrated under pressure. Thereafter, Compound 10a was obtained in a yield of 65% using MPLC (Biotage SNAP HP-Sil column).

R$_f$=(3:7 ethyl acetate:hexane). $^1$H NMR (400 MHz, MeOD) δ 7.26 (s, 1H), 6.77 (s, 1H), 6.15-6.02 (m, 2H), 5.51 (d, J=17.2 Hz, 1H), 5.43 (d, J=17.2 Hz, 1H), 5.32 (t, J=11.2 Hz, 11.2 Hz, 2H), 4.68 (dd, J=17.2 Hz, 4.4 Hz, 4H), 3.70 (t, J=6.8 Hz, 6.8 Hz, 2H), 3.33 (s, 2H), 2.02-1.89 (m, 4H). $^{13}$C NMR (100 MHz, MeOD) δ 167.2, 155.7, 154.2, 132.8, 132.6, 128.4, 119.8, 116.7, 116.4, 114.1, 99.41, 69.4, 69.2, 45.7, 33.4, 25.4, 24.2

6 (2,4-bis(allyloxy)-5-chlorophenyl)(piperidin-1-yl)methanone (10b)

Compound 9 (0.30 g, 1.12 mmol), piperidine (0.12 ml, 1.23 mmol), N,N'-dicyclohexylcarbodiimide (0.46 g, 2.23 mmol), 1-hydroxybenzotriazole (0.15 g, 1.12 mmol) and N,N-diisopropylethylamine (0.19 mL, 1.12 mmol) were dissolved in 4 ml of DMF, and stirred at 120° C. for 3 hours under microwave irradiation (Biotage Initiator).

The mixture was dissolved in ethyl acetate and the organic layer was washed with water, dried over Na$_2$SO$_4$ and concentrated under pressure. Thereafter, Compound 10b was obtained in a yield of 44% using MPLC (Biotage SNAP HP-Sil column).

R$_f$=0.21 (3:7 ethyl acetate:hexane). $^1$H NMR (400 MHz, CDCl$_3$) δ 7.23 (s, 1H), 6.67 (s, 1H), 6.06-5.92 (m, 2H), 5.44

(d, J=17.6 Hz, 1H), 5.37 (d, J=17.2 Hz, 1H), 5.31 (d, J=10.8 Hz, 1H), 5.26 (d, J=10.4 Hz, 1H), 5.59 (d, J=4.8 Hz, 2H), 4.52 (t, J=4.4 Hz, 5.2 Hz, 2H), 3.66 (dd, J=17.2 Hz, 1.6 Hz, 1H), 3.19 (dd, J=12.0 Hz, 7.6 Hz, 2H), 1.614 (s, 4H), 1.48 (d, J=42.8 Hz, 2H). $^{13}$C NMR (100 MHz, CDCl$_3$) δ 166.3, 155.3, 154.0, 132.8, 132.5, 129.4, 120.3, 118.3, 117.9, 115.2, 99.9, 70.2, 69.8, 48.2, 42.9, 26.5, 25.8, 24.7.

7. (2,4-bis(allyloxy)-5-chlorophenyl)(morpholino) methanone (10c)

Compound 9 (0.50 g, 1.85 mmol), morpholine (0.18 ml 2.04 mmol), N,N'-dicyclohexylcarbodiimid (0.76 g, 3.70 mmol), 1-hydroxybenzotriazole (0.55 g, 1.85 mmol) and N,N-diisopropylethylamine (0.32 mL, 1.85 mmol) were dissolved in 4 mL of DMF and stirred at 120° C. for hours under microwave irradiation.

The mixture was dissolved in ethyl acetate and the organic layer was washed water, dried over Na$_2$SO$_4$, and concentrated under pressure. Thereafter, Compound 10c was obtained in a yield of 68% using MPLC (Biotage SNAP HP-Sil column).

R$_f$=0.20 (4:6 ethyl acetate:hexane). R$_f$=0.21 (3:7 ethyl acetate:hexane). $^1$H NMR (400 MHz, CDCl$_3$) δ 7.27 (s, 1H), 6.47 (s, 1H), 6.07-5.93 (m, 2H), 5.44 (dd, J=17.2 Hz, 1.2 Hz, 1H), 5.36 (dd, J=17.2 Hz, 1.6 Hz, 1H), 5.32 (dd, J=4 Hz, 2.8 Hz, 2H), 5.29 (dd, J=10.4 Hz, 1.2 Hz, 2H), 4.56 (dd, J=30.8 Hz, 4.0 Hz, 4H).

8. (2,4-bis(allyloxy)-5-chlorophenyl)(4-methylpiperazin-1-yl)methanone 10e)

Compound 9 (0.30 g, 1.12 mmol), 1-methylpiperazine (0.19 ml, 1.67 mmol), N,N'-dicyclohexylcarbodiimide (0.46 g, 2.23 mmol) 1-hydroxybenzotriazole (0.15 g, 1.12 mmol) and N,N-diisopropylethylamine (0.19 mL, 1.12 mmol) were dissolved in 4 mL of DMF and stirred at 120° C. for 3 hours under microwave irradiation (Biotage Initiator).

The mixture was dissolved in ethyl acetate and the organic layer was washed with water, dried over Na$_2$SO$_4$ and concentrated under pressure. Thereafter Compound 10e was obtained in a yield of 64% using MPLC (Biotage SNAP HP-Sil column).

R$_f$=0.14 (9:1 ethyl acetate:methanol). $^1$H NMR (400 MHz, CDCl$_3$) δ 7.24 (s, 1H), 6.46 (s, 1H), 6.06-5.90 (m, 2H), 5.43 (dd, J=17.2 Hz, 1.2 Hz, 1H), 5.34 (dd, J=17.2 Hz, 1.2 Hz, 1H), 5.30 (dd, J=10.4 Hz, 0.8 Hz, 1H), 5.25 (dd, J=10.4 Hz, 1.2 Hz, 1H), 4.58 (d, J=4 Hz, 2H), 4.50 (s, 2H), 3.76 (d, J=61.6 Hz, 2H), 3.27 (d, J=15.2 Hz, 2H), 2.27 (d, J=35.2 Hz, 4H), 2.27 (s, 3H). $^{13}$C NMR (100 MHz, CDCl$_3$) δ 166.4, 155.5, 154.0, 132.5, 132.4, 129.6, 119.4, 118.3, 118.1, 115.2, 99.6, 70.1, 69.8, 55.3, 54.8, 46.9, 46.2, 41.8.

9. 1-(4-(2,4-bis(allyloxy)-5-chlorophenyl)piperazin-1-yl)ethanone (10f)

Compound 9 (0.30 g, 1.12 mmol), 1-ethylpiperazine (0.21 ml, 1.67 mmol), N,N'-dicyclohexylcarbodiimide (0.46 g, 2.23 mmol) 1-hydro benzotriazole (0.15 g, 1.12 mmol) and N,N-diisopropylethylamine (0.19 mL, 1.12 mmol) were dissolved in 4 mL, of DMF and stirred at 120° C. for 3 hours under microwave irradiation (Biotage Initiator).

The mixture was dissolved in ethyl acetate and the organic laser was washed with water, dried over Na$_2$SO$_4$ and concentrated under pressure. Thereafter, Compound 10f was obtained in a yield of 86% using MPLC (Biotage SNAP HP-Sil column).

R$_f$=0.20 (9:1 ethyl acetate:methanol). $^1$H NMR (400 MHz, CDCl$_3$) δ 7.25 (s, 1H), 6.46 (s, 1H), 6.04-5.93 (m, 2H), 5.42 (dd, J=17.2 Hz, 1.2 Hz, 1H), 5.32 (d, J=15.1 Hz, 1H), 5.26 (d, J=14.4 Hz, 2H), 4.54 (d, J=32.8 Hz, 2H), 3.77-3.18 (m, 8H), 2.07 (d, J=23.6 Hz, 3H).

10. (5-chloro-2,4-dihydroxyphenyl) (pyrrolidin-1-yl) methanone (11a)

Compound 10a (0.23 g, 0.72 mmol) was stirred in the presence of PdCl$_2$(PPh$_3$)$_2$ (23 mg) and 4 ml of ammonium formate in THF (150 mg) at 120° C. for 30 min under microwave irradiation.

The reaction mixture was diluted with ethyl acetate and the organic layer was washed with water. It was dried over Na$_2$SO$_4$, concentrated under pressure to obtain Compound 11a by using MPLC in yield of 29%.

R$_f$=0.26 (3:7 ethyl acetate:hexane). $^1$H NMR (400 MHz, CDCl$_3$) δ 7.20 (s, 1H), 6.29 (s, 1H), 4.24 (s, 2H), 3.15 (t, J=1.6 Hz, 1.6 Hz, 4H), 1.77 (t, J=6.4 Hz, 6.8 Hz, 4H). $^{13}$C NMR (100 MHz, CDCl$_3$) δ 169.0, 158.9, 156.3, 129.4, 111.5, 110.9, 104.2, 49.3, 49.1, 48.3, 48.1.

11. (5-chloro-2,4-dihydroxyphenyl) (piperidin-1-methanone (11b)

Compound 10h (0.17 g, 0.50 mmol) seas stirred in the presence of PdCl$_2$(PPh$_3$)$_2$ (17 mg) and 4 ml of ammonium formate in THF (150 mg) at 120° C. for 30 minutes under microwave irradiation.

The reaction mixture was diluted with ethyl acetate and the organic layer was washed with water. It was dried over Na$_2$SO$_4$, concentrated under pressure and then Compound 11h was obtained in a yield of 28% using MPLC.

R$_f$=0.27 (5:5 ethyl acetate:hexane). $^1$H NMR (400 MHz, MeOD) δ 7.04 (s, 1H), 6.42 (s, 1H), 3.45 (s, 4H), 1.62 (d, J=4.8 Hz, 2H), 1.55 (d, J=4.4 Hz, 4H). $^{13}$C NMR (100 MHz, MeOD) δ 169.2, 156.0, 154.9, 129.8, 116.9, 112.2, 104.4, 36.8, 34.5, 26.8, 25.2

12. (5-chloro-2,4-dihydroxyphenyl) (morpholino)methanone (11c)

Compound 10c (0.42 g, 1.25 mmol) was stirred in the presence of PdCl$_2$(PPh$_3$)$_2$ (42 g) and 4 ml of ammonium formate in THF (150 mg) at 120° C. for 30 minutes under microwave irradiation.

The reaction mixture was diluted with ethyl acetate and the organic layer was washed with water. It was dried over Na$_2$SO$_4$, concentrated under pressure and then Compound 11c was obtained in a yield of 49% using MPLC.

R$_f$=0.24 (4:6 ethyl acetate:hexane). $^1$H NMR (400 MHz, MeOD) δ 7.16 (s, 1H), 6.48 (s, 1H), 3.69 (d, J=4.0 Hz, 4H), 3.57 (s, 4H)

13. (5-chloro-2,4-dihydroxyphenyl)(4-methylpiperazin-1-yl)methanone (11e)

Compound 10e (0.25 g, 0.72 mmol) was stirred in the presence of PdCl$_2$(PPh$_3$)$_2$ (25 mg) and 4 ml of ammonium formate in THF (150 mg) at 120° C. for 30 minutes under microwave irradiation.

The reaction mixture was diluted with ethyl acetate and the organic layer was washed with water. It was dried over Na$_2$SO$_4$, concentrated lender pressure and then Compound 11e was obtained in two steps in a yield of 30% using MPLC.

$R_f$=0.20 (7:3 ethyl acetate:Methanol). $^1$H NMR (400 MHz, MeOD) δ 7.13 (s, 1H), 6.47 (s, 1H), 3.59 (d, J=8.0 Hz, 6H), 3.52 (s, 2H) 2.10 (s, 3H). $^{13}$C NMR (125 MHz, DMSO) δ 165.9, 154.4, 153.4, 128.9, 116.0, 109.9, 103.5, 54.5, 45.6, 40.4

14. 1-(4-(5-chloro-2,4-dihydroxybenzol)piperazin-1-yl)ethanone (11f)

Compound 10f (0.17 g, 0.45 mmol)) stirred in the presence of $PdCl_2(PPh_3)_2$ (17 mg) and 4 ml of ammonium formate in THF (150 mg) at 120° C. for 30 minutes under microwave irradiation.

The reaction mixture was diluted with ethyl acetate and the organic layer was washed with water. It was dried over $Na_2SO_4$, concentrated under pressure and then compound 11f was obtained in two steps in a yield of 61% using MPLC.

$R_f$=0.14 (9:1 ethyl acetate:Methanol). $^1$H NMR (400 MHz, MeOD) δ 7.14 (s, 1H), 6.46 (s, 1H), 3.60 (s, 4H), 2.51 (t, J=4.8 Hz, 4.8 Hz, 4H), 2.35 (s, 3H). $^{13}$C NMR (125 MHz, DMSO) δ 168.4, 166.2, 154.5, 153.4, 129.2, 115.9, 110.1, 103.5, 45.7, 40.9, 21.2

15. 5-chloro-2,4-dihydroxybenzoic Acid (18)

Compound 7 (1.98 g, 9.76 mmol) and 30 ml of methanol-30 ml of sodium hydroxide in $H_2O$ (6 g) were stirred at room temperature for 24 hours. The mixture was neutralized with 3N HCl to pH 6 and extracted three times with ethyl acetate.

The organic layer was dried over $Na_2SO_4$ and concentrated under reduced pressure to obtain Compound 18 in a yield of 100%.

$^1$H NMR (400 MHz, CDCl$_3$) δ 7.75 (s, 1H), 6.40 (s, 1H). $^{13}$C NMR (100 MHz, CDCl$_3$) δ 171.5, 162.0, 158.9, 131.5, 112.1, 105.8, 103.6.

16. (5-chloro-2,4-dihydroxyphenyl) (piperazin-1-yl)methanone (11d)

Compound 18 (0.21 g, 1.13 mmol), test-butyl 1-piperazinecarboxylate (0.32 g, 1.69 mmol), 1-ethyl-3-(3-dimethylaminopropyl)carbodiimide (0.46 g, 2.26 mmol), N,N'-dicyclohexylcarbodiimide (0.46 g, 2.23 mmol), and 1-hydroxybenzotriazole (0.15 g, 1.13 mmol) and N,N-diisopropylethylamine (0.20 mL, 1.13 mmol) were dissolved in 4 ml of DMF, and stirred at 120° C. for 3 hours under microwave irradiation.

The mixture was dissolved in ethyl acetate and the organic layer was washed with 1 N—HCl solution, dried over $Na_2SO_4$, and concentrated under pressure. Thereafter, an intermediate compound was synthesized in a yield of 69% using MPLC, (Biotage SNAP HP-Sil column).

$R_f$=0.23 (5:5 ethyl acetate:hexane).

The intermediate compound was stirred for 24 hours at room temperature ire the presence of 10 ml of 6N HCl solution and 10 ml of THF. After diluting the reaction with ethyl acetate, the organic layer was washed with water, dried over $Na_2SO_4$, and concentrated under pressure. It as purified by MPLC to obtain Compound 11d in two steps in a yield of 32%.

$^1$H NMR (400 MHz, MeOD) δ 7.13 (s, 1H), 6.45 (s, 1H), 6.45 (s, 1H), 6.74 (s, 4H), 3.21 (d, J=4.4 Hz, 4H). $^{13}$C NMR (100 MHz, MeOD) δ 169.7, 157.1, 155.2, 131.0, 115.5, 113.2, 104.7, 62.9, 44.7

17. 4-(5-chloro-2,4-dihydroxybenzoyl)piperazin-2-one (11 g)

Compound 18 (0.30 g, 1.12 mmol), piperidine (0.12 ml, 1.23 mmol), N,N'-dicyclohexylcarbodiimide (0.46 g, 2.23 mmol), 1-hydroxybenzotriazole (0.15 g, 1.12 mmol) and N,N-diisopropylethylamine (0.19 mL, 1.12 mmol) were dissolved in 4 ml of DMF and stirred at 120° C. for 3 hours under microwave irradiation.

The reaction mixture was diluted with ethyl acetate and the organic layer was washed with water. It was dried over $Na_2SO_4$, concentrated under pressure and Compound 11g was obtained in a yield of 44% using MPLC.

$R_f$=0.21 (3:7 ethyl acetate:hexane). $^1$H NMR (400 MHz, DMSO) δ 10.07 (s, 1H), 8.04 (s, 1H), 7.09 (s, 1H), 6.55 (s, 1H), 3.92 (s, 2H), 3.53 (s, 2H), 3.36 (s, 3H), 3.19 (s, 2H)

18. 1-(5-chloro-2,4-dihydroxybenzoyl) pyrrolidin-3-one (11h)

Compound 18 (0.05 g, 0.27 mmol), 3-pyrrolidinone hydrochloride (0.05 g, 0.41 mmol), 1-ethyl-3-(3-dimethylaminopropyl)carbodiimide (0.11 g, 0.55 mmol), 1-hydroxybenzotriazole (0.04 g, 0.27 mmol), N,N'-diisopropylethylamine (0.20 mL, 1.13 mmol) and N,N'-dicyclohexylcarbodiimide (0.10 mL, 0.55 mmol) were dissolved in 4 m of DMF and stirred at 120° C. for 3 hours under microwave irradiation (Biotage Initiator).

The organic layer was washed with 1N—HCl solution, dried over $Na_2SO_4$, concentrated under pressure and purified by MPLC to obtain Compound 11h in a yield of 10%.

$R_f$=0.21 (5:5 ethyl acetate:hexane). $^1$H NMR (400 MHz, CDCl$_3$) δ 11.04 (s, 1H), 7.39 (s, 1H), 6.66 (s, 1H), 5.93 (s, 1H), 4.21 (t, J=8.0 Hz, 7.6 Hz, 2H), 4.14 (s, 2H), 2.67 (t, J=7.6 Hz, 8.0 Hz, 2H).

19. 1-(5-chloro-2,4-dihydroxybenzoyl)piperidin-4-one (11i)

Compound 18 (0.20 g, 1.09 mmol), 4-piperidine (0.25 g, 1.63 mmol), 1-ethyl-3-(3-dimethylaminopropyl) (0.42 g, 2.17 mmol), 1-hydroxybenzotriazole (0.15 g, 1.09 mmol) and N,N-diisopropylethylamine (0.39 mL, 2.17 mmol) wore dissolved in 4 ml of DMF and stirred at 120° C., for 3 hours under a microwave irradiation (Biotage Initiator).

The reaction mixture was diluted with ethyl acetate and the organic layer was washed with 1 N HCl solution. It was dried over $Na_2SO_4$, concentrated under pressure and then Compound 11i was obtained in a yield of 3% by using MPLC.

$R_f$=0.21 6:4 ethyl acetate:hexane). $^1$H NMR (400 MHz, CDCl$_3$) δ 10.14 (s, 1H), 7.31 (s, 1H), 6.67 (s, 1H), 5.88 (s, 1H), 3.97 (t, J=6.4 Hz, 6.0 Hz, 4H), 2.58 (t, J=6.0 Hz, 6.4 Hz, 4H).

20. (5-chloro-2,4-dihydroxyphenyl)(4-methyl-2-phenylpiperazin-1-yl)methanone (11j)

Compound 18 (0.20 g, 1.05 mmol), 1-methyl-3-phenylpiperazine (0.28 g, 1.58 mmol), 1-ethyl-3-(3-dimethylaminopropyl) (0.40 g, 2.10 mmol), 1-hydroxybenzotriazole (0.14 g, 1.05 mmol) and N,N-diisopropylethylamine (0.19 mL, 1.05 mmol) were dissolved in 4 ml of DMF and stirred at 120° C. for 3 hours under a microwave irradiation (Biotage Initiator).

The reaction mixture was diluted with ethyl acetate and the organic layer was washed with 1 N HCl solution. It was dried over $Na_2SO_4$, concentrated under pressure and purified by MPLC to obtain Compound 11j in a yield of 23%.

$R_f$=0.21 (8:2 ethyl acetate:hexane). $^1$H NMR (400 MHz, $CDCl_3$) δ 7.46 (d, J=4.4 Hz, 2H), 7.37 (t, J=7.2 Hz, 7.2 Hz, 2H), 7.27 (t, J=7.2 Hz, 6.8 Hz, 1H), 7.17 (s, 1H), 6.61 (s, 1H), 5.58 (s, 1H), 4.24 (s, 1H), 3.24 (d, J=12.0 Hz, 1H), 3.22 (t, J=12.4 Hz, 10.4 Hz, 1H), 2.81 (d, J=10.8 Hz, 1H), 2.50 (dd, J=12.0 Hz, 4.0 Hz, 1H), 2.32 (s, 3H), 2.21-2.14 (m, 1H).

21. Methyl 2,4-dihydroxy-5-isopropylbenzoate (12)

Compound 6 (3.9 g, 23.0 mmol), 2-bromopropane (4.3 mL, 46.0 mmol) and aluminum chloride (6.1 g, 46.0 mmol) were dissolved in $CH_2Cl_2$ and then stirred under argon at 50° C. for 24 hours with a reflux condenser under a microwave irradiation (Biotage Initiator).

3-Bromopropane (4.3 ml, 46.0 mmol) was added to the reaction mixture three times every 6 hours.

The mixture was neutralized with 10% NaOH to pH 5, concentrated under pressure and extracted with ethyl acetate.

The organic layer was washed with saturated $NaHCO_3$ solution three times, dried over $Na_2 SO_4$, concentrated under pressure and purified by column to obtain Compound 12 in a yield of 45%.

$R_f$=0.21 (1:4 ethyl acetate:hexane). $^1$H NMR (400 MHz, $CDCl_3$) δ 10.8 (s, 1H), 7.64 (s, 1H), 6.34 (s, 1H), 5.53 (s, 1H), 3.92 (s, 3H), 3.15-3.08 (m, 1H), 1.25 (d, J=10.8 Hz, 6H). $^{13}$C NMR (100 MHz, $CDCl_3$) δ 170.7, 161.6, 159.6, 128.1, 127.1, 105.7, 103.2, 52.2, 26.7, 22.8

22. Methyl 2,4-bis(allyloxy)-5-isopropylbenzoate (13)

Compound 12 (2.1 g, 10.3 mmol), allyl bromide (2.3 mL, 26.8 mmol) and potassium carbonate (3.7 g, 26.8 mmol) were dissolved in DMF and stirred for 18 hours.

The mixture was diluted with ethyl acetate and the organic layer was washed with $H_2O$, dried over $Na_2SO_4$, and concentrated under pressure to obtain Compound 13 in a yield of 84%.

$^1$H NMR (400 MHz, $CDCl_3$): δ 7.71 (s, 1H), 6.41 (s, 1H), 6.10-5.97 (m, 2H), 5.50 (dd, J=17.2 Hz, 1.6 Hz, 1H), 5.41 (dd, J=17.2 Hz, 1.2 Hz, 1H), 5.27 (d, J=10.8 Hz, 2H), 4.56 (dd, J=9.6 Hz, 4.8 Hz, 4H), 3.84 (s, 1H), 3.26-3.19 (m, 1H), 1.19 (d, J=6.8 Hz, 6H).

23. 2,4-bis(allyloxy)-5-isopropylbenzoic Acid (14)

Compound 13 (2.5 g, 8.6 mmol) and 30 ml of methanol-30 ml of sodium hydroxide in $H_2O$ (1.7 g, 43.1 mmol) were stirred at room temperature for 24 hours.

The mixture was diluted with ethyl acetate and the organic layer was washed with 3N HCl solution and dried over $Na_2SO_4$, concentrated under pressure and purified using a column to obtain Compound 14 in a yield of 58%.

$R_f$=0.18 (1:4 ethyl acetate:hexane). $^1$H NMR (400 MHz, $CDCl_3$): δ 7.97 (s, 1H), 6.43 (s, 1H), 6.10-5.97 (m, 2H), 5.47-5.39 (m, 2H), 5.30 (d, J=10.8 Hz, 2H), 4.73 (d, J=5.6 Hz, 2H), 4.57 (d, J=4.8 Hz, 2H), 3.26-3.19 (m, 1H), 1.18 (d, J=6.8 Hz, 6H).

24. (2,4-bis(allyloxy)-5-isopropylphenyl)(4-methyl-2-phenylpiperazin-1-yl)methanone (16)

Compound 14 (0.18 g, 0.66 mmol), 1-methyl-3-phenylpiperazine (0.18 g, 0.99 mmol), 1-ethyl-3-(3-dimethylaminopropyl) (0.25 g, 1.33 mmol), 1-hydroxybenzotriazole (0.09 g, 0.66 mmol) and N,N-diisopropylethylamine (0.09 mL, 0.66 mmol) were dissolved in 4 ml of DMF and stirred at 120° C. for 3 hours under a microwave irradiation (Biotage Initiator).

The reaction mixture was diluted with ethyl acetate and the organic layer was washed with 1 N HCl solution. It was dried over $Na_2SO_4$, concentrated under pressure and purified by MPLC to obtain Compound 16 in a yield of 92%.

$R_f$=0.24 (3:7 ethyl acetate:hexane).

25. (2,4-dihydroxy-5-isopropylphenyl)(4-methyl-2-phenylpiperazin-1-yl)methanone (17)

Compound 16 (0.26 g, 0.61 mmol) was stirred under microwave irradiation in the presence of $PdCl_2(PPh_3)_2$ (10 mg) and 4 ml of ammonium formate in THF (227 ma) at 120° C. for 30 minutes.

The reaction mixture was diluted with ethyl acetate and the organic layer was washed with water. It was dried over $Na_2SO_4$, concentrated under pressure and then Compound 17 was obtained in two steps in a yield of 15% using MPLC.

$R_f$=0.32 (8:2 ethyl acetate:Hexane). $^1$H NMR (400 MHz, $CDCl_3$): 7.45 (d, J=7.6 Hz, 2H), 7.37 (t, J=7.2 Hz, 7.6 Hz, 2H), 7.25(t, J=7.8 Hz, 7.6 Hz, 1H), 6.99 (s, 1H), 6.40 (s, 1H), 5.58 (s, 1H), 4.24 (s, 1H), 3.44 (t, J=8.8 Hz, 12.0 Hz, 1H), 3.30 (t, J=12.4 Hz, 10.4 Hz, 1H), 3.05-3.00(m, 1H), 2.79 (d, J=10.8 Hz, 1H), 2.47 (dd, J=12.0 Hz, 4.0 Hz, 1H), 2.30 (s, 3H), 2.22-2.16 (m, 1H), 0.95 (dd, J=20.0 Hz, 6.0 Hz, 6H). $^{13}$C NMR (100 MHz, $CDCl_3$) δ 171.5, 158.1, 138.8, 128.9, 127.3, 127.1, 126.4, 109.1, 103.9, 60.6, 55.4, 45.6, 26.1, 22.5, 21.1, 19.9, 14.3

EXAMPLE 2

Evaluation of Biological Activity of Dihydroxyphenyl Compound

1. Confirmation of HSP90 Inhibitory Effect

The HSP90 inhibitory effect of the dihydroxyphenyl compound synthesized in the Example 1 was confirmed by a Fluorescence Polarization assay (FP assay), HFB buffer (100 mM HEPES (4-(2-hydroxyethyl)-1-piperazineethanesulfonic acid) pH 7.3, 2 M KCl, 1 M $MgCl_2$, 1 M $Na_2MoO_4$, 100% $NP_4O$), HSP90α N-terminal domain (2 μM) protein, FITC (fluorescein isothiocyanate)-labeled geldanamycin (GA) inhibitor (500 nM) and Compounds at concentrations of (0.001, 0.01, 0.1, 0.5, 1, 5, 10, 50, 100 μM) were added to each well.

Thereafter, plates were incubated at 4° C. for 14 hours. The polarization values of the millipolarization units were measured at an excitation wavelength of 495 nm and an emission wavelength of 530 nm.

All experimental data were analyzed using Prism software (version 5.0, Graphpad Software, San Diego, Calif.). In addition, tPSA (Topological Polar Surface Area) calculated using Cherndraw software and the measured values of Log P are shown in Tables 1 and 2 below.

[Chemical Formula 3]

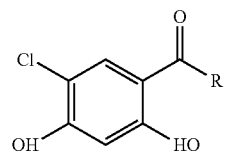

Compounds 11a to 11i are represented by the Chemical Formula 3.

TABLE 1

| Entry | R | Compound | HSP90 (FP) (IC$_{50}$; μM) | Inhibition rate at 10 μM (%) | Inhibition rate at 30 μM (%) | tPSA | LogP |
|---|---|---|---|---|---|---|---|
| 1 | pyrrolidine | 11a | 0.348 | 8.1 | 22.1 | 60.7 | 1.13 |
| 2 | piperidine | 11b | 0.541 | 7.6 | 26.3 | 60.7 | 1.69 |
| 3 | morpholine | 11c | 0.383 | 24.3 | 44.0 | 70 | 0.66 |
| 4 | piperazine | 11d | 5.59 | 0 | 0 | 72.8 | 0.65 |
| 5 | N-methylpiperazine | 11e | 0.253 | 26.3 | 48.7 | 64 | 1.23 |
| 6 | N-acetylpiperazine | 11f | 3.21 | 0 | 10.5 | 81.1 | 0.25 |
| 7 | piperazin-2-one | 11g | 1.37 | 0 | 0 | 89.9 | 0.45 |
| 8 | 3-oxopyrrolidine | 11h | 3.92 | 0 | 0 | 77.8 | 0.84 |
| 9 | 4-oxopiperidine | 11i | 0.670 | 12.5 | 48.2 | 77.8 | 0.6 |

[Chemical Formula 4]

Compounds 11j and 17 are represented by the above Chemical Formula 4.

TABLE 2

| Entry | R | compound | HSP90(FP) (IC$_{50}$; μM) | Inhibition rate at 10 μM (%) | Inhibition rate at 30 μM (%) | tPSA | LogP |
|---|---|---|---|---|---|---|---|
| 10 | Cl | 11j | 0.070 | — | — | 64.01 | 3.22 |
| 11 | (i-propyl) | 17 | 0.0495 | 72.08 | 77.58 | 64.01 | 3.80 |

As a result, as shown in the Table 2, Compound 17 showed an IC$_{50}$ of 0.0495 μM for HSP90 and an IC$_{50}$ of 98 μM for H1975.

In addition, HSP90 inhibitory activity of by Compound 17 confirmed by FP analysis is shown in FIG. 1. The increased concentration of Compound 17 added FITC-geladinomycin/HSP90α (N-terminal domain) protein response and recorded FP readings.

As shown in the Table 2, Compound 17 showed HSP90 inhibitory activity in a concentration-dependent manner.

2. Confirmation of Cell Proliferation and Survival Inhibition

Next, non-metastatic lung cancer cells were treated with Compound 17 and the cell proliferation rate or cell survival rate was measured by MTS [3-(4,5-dimethylthiazol-2-yl)-5-(3-carboxymethoxyphenyl)-1-2H-tetrazolium, inner salt] analysis.

Cells were dispensed in 96-well plates at 3000 cell/well (Sk-Br3) and 2000 cell/well (H1975), and 100 μL of the medium was added per well and then was incubated overnight.

The following day, Compound 17 at a concentration of 0, 0.01, 0.1, 1, 5, 10, 30, 50 or 70 μM or 1% DMSO vehicle (control) was added to each well, and cultured at 37° C. for 1, 2 and 3 days.

Cell proliferation was evaluated using the Promega Cell Titer 96 Aqueous One Solution cell proliferation assay.

After compound and cell culture, 20 μL of assay substrate solution was added to each well and incubated at 37° C. for an additional 1 hour.

Cell proliferation was confirmed by measuring the absorbance at 490 nm using a microplate reader (Tecan Infinite F200 Proplate reader).

Compound 17 at a concentration of 0, 0.01, 0.1, 1, 5, 10, 30, 50 or 70 μM or 1% DMSO vehicle (control group) was added to each well and incubated at 37° C. for 72 hours and the absorbance was measured at 490 nm and the measured value was expressed as a percentage of the absorbance of the cells cultured only with DMSO to confirm cell survival.

Figure 2:
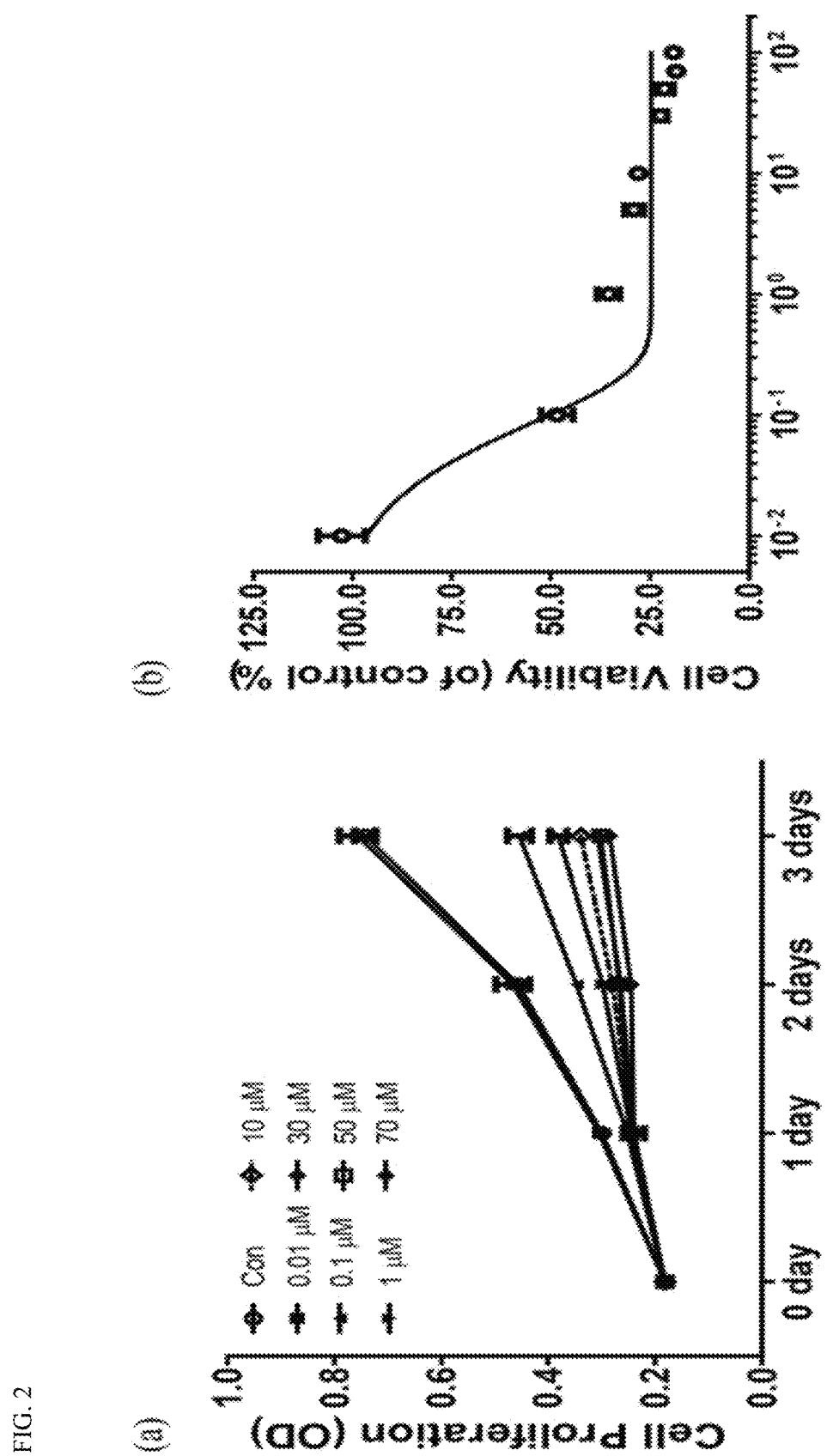
FIG. 2 illustrates (A) showing the results of inhibiting the proliferation rate of non-small cell lung cancer cells by various concentrations of Compound 17, and (B) showing a result of confirming the inhibition of survival of non-small cell lung cancer cells.

As a result, as shown in FIG. 2, as time passed, the proliferation rate of the cells was inhibited in a concentration-dependent manner of Compound 17 (FIG. 2A), and cell death was also observed (FIG. 2B).

3. Confirmation of H1975 Colony Formation Inhibitory Effect

H1975 cells were treated with Compound 17 at a concentration of 0.05 or 0.5 μM for 3 weeks and then clogenic assay was performed.

First, RPMI1640 medium (10% FBS, 0.48% agar) was added to a 6-well plate and hardened, and then, 10000 cells (H1975) were dispensed in a medium containing RPMI1640 medium (10% FBS, 0.33% agar) and solidified. After solidification, the cells were treated with compound at a concentration of 0.05 or 0.5 nM for 24 hours, followed by culturing for 3 weeks, and then colony formation was confirmed using a crystal violet staining solution.

Figure 3:
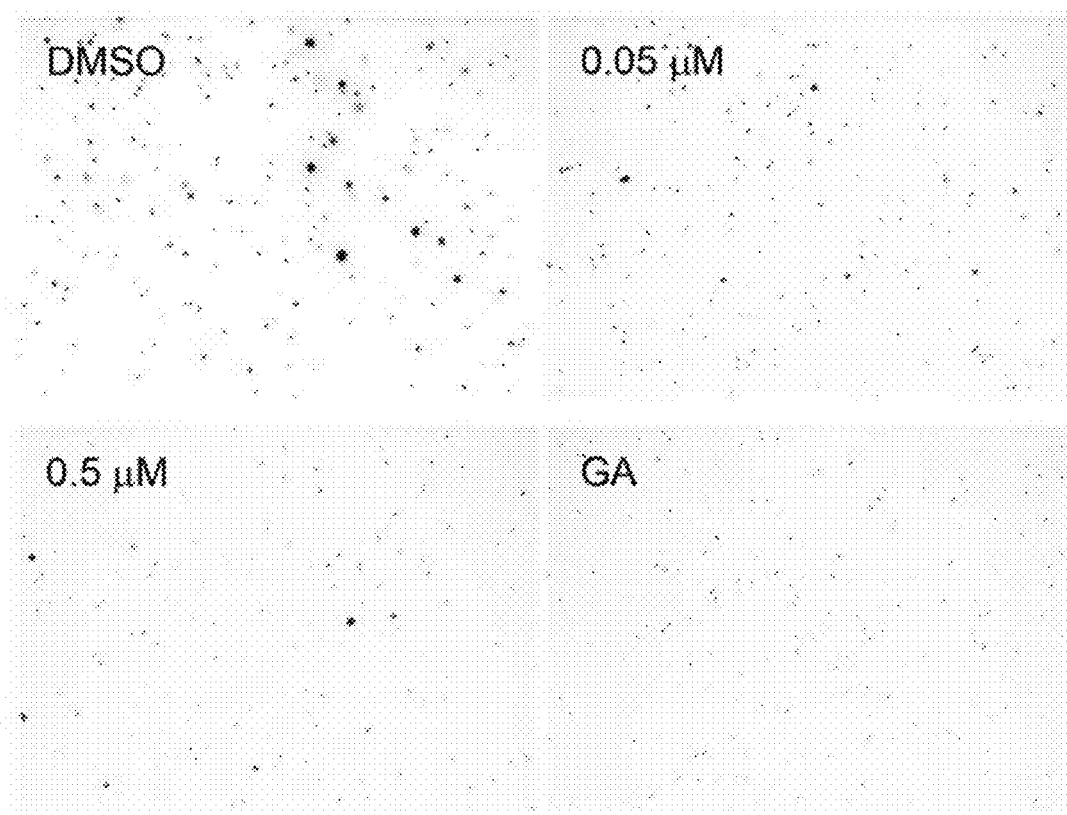
FIG. 3 shows the results of inhibition of colony formation of non-small cell lung cancer cells of Compound 17 at various concentrations.

As a result, as shown in FIG. 3, Compound 17 inhibited the colony formation of H1975 even at a low concentration of 0.05 M.

4. Protein Expression Analysis

Recombinant HSP90 was expressed from pET-15b plasmid (Novagen) into *Escherichia coli* BL21 (DE3) cells (BioLabs).

The new colony was grown with shaking at a speed of 180 rpm until the absorbance reached A$_{600}$=0.5 using LB broth medium containing 2.5 mg mL: (500 μl/200 ml) of ampicillin.

Thereafter, protein expression was induced by isopropyl-1-thio-β-D-galactopyranoside (final concentration 1 mM).

After decreasing the temperature to 18° C., the cells were incubated overnight with shaking to obtain cell pellet by centrifugation (4000 rpm, 20 min, 4° C.).

The cell pellet was suspended in NTA (nitrilotriacetate acid) buffer (containing 20 mM Tris pH 8.0, 0.5 M NaCl), sonicated in ice and centrifuged to obtain supernatant (14000 rpm, 99 min, 4° C.).

The His-tagged protein was purified with a Histidine Trap column and nickel-nitriloacetic acid and separated by FPLC (Fast Protein Liquid Chromatography: Phamacia).

To identify HSP proteins, proteins were analyzed by western blotting.

Salts were removed from the purified protein by the PD10 column and concentrated to 2.4 mg/ml in Vivaspin 20 and stored at −70° C.

Next, the cells were dispensed into 100 mm culture dishes (1×10$^6$/dish) and adhered to the bottom surface overnight. Compound 17 at a concentration of 0.05, 0.1, 0.5 or 1 μM was added to the cells, followed by further culture for 24 hours.

In addition, cells were treated with DMSO (1%) or geladinamycin (1 μM) as a control and cultured for 24 hours.

The cultured cells were harvested and lysed in ice-cold lysis buffer (23 mM Tris-HCl pH 7.6, 130 mM NaCl, 1% NP40, % sodium deoxycholate, 0.1% SDS (sodium dodecylsulfate)), and 30 μg of the lysate was separated by SDS-PAGE (SDS-polyacrylamide gel electrophoresis) and transferred to a PVDF membrane (Bio-Rad).

Membranes were blocked with TBST (Tween 20 containing tris-Buffered Saline) containing 5% skim milk and incubated with the respective primary antibodies [EGFR (Epidermal growth factor receptor), Her2 (human epidermal growth factor receptor type 2), Met, N-cadherin, E-cadherin, α-tubulin, acetyl-α-tubulin, protein kinase B (Akt), c-Raf, Cdk4 (Cyclin-dependent kinase 4), HSP90, HSP70, PARP (Poly ADT-ribose Polymerase), caspase 3, cleaved caspase 3, truncated caspase 8, B-cell lymphoma 2 (Bcl-2). Bax or β-Actin, purchased from Cell Signaling Technology (USA)].

After binding to a secondary antibody conjugated with horseradish peroxidase, the protein was visualized by ECL (electrochemiluminescence, GE healthcare, USA).

Figure 4:
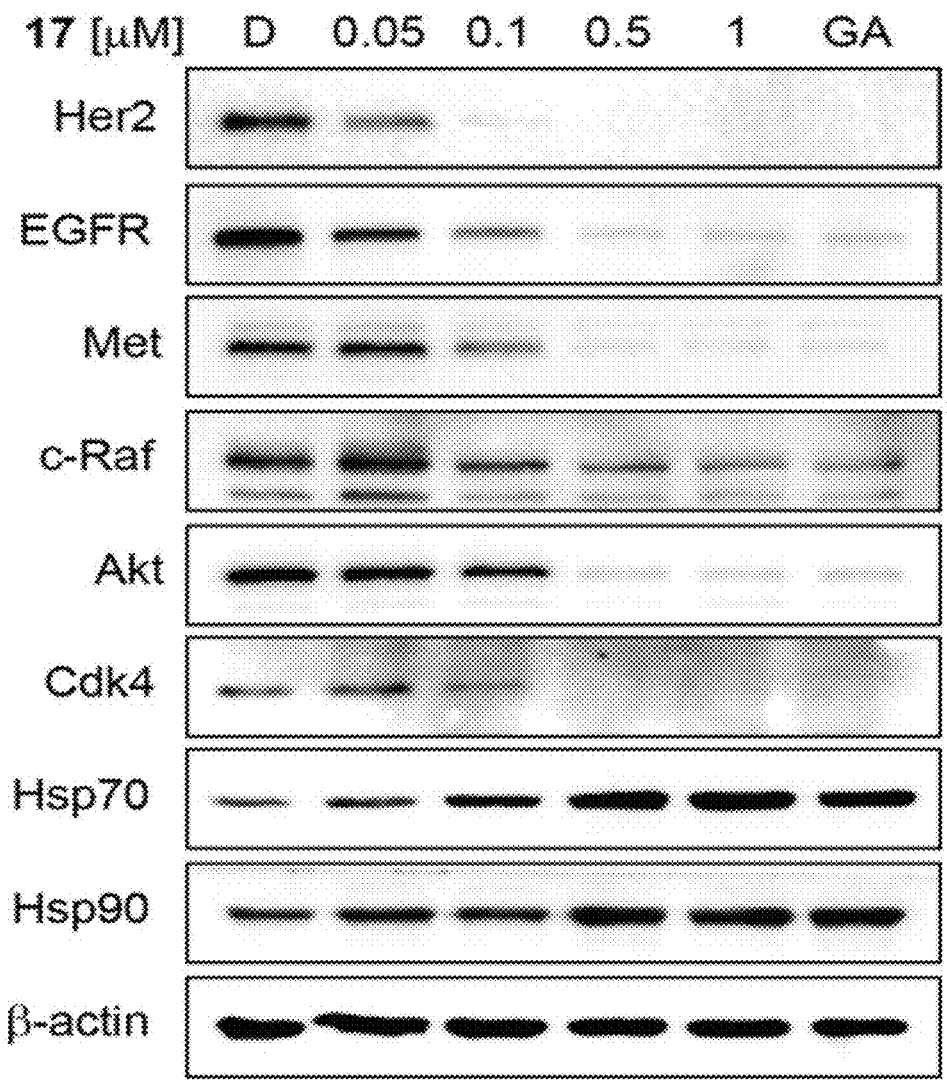
FIG. 4 shows the results of changes in protein expression after treating Compound 17 having various concentrations on non-small cell lung cancer cells.

As a result, as shown in FIG. 4, Compound 17 inhibited HSP protein in concentration-dependent manner to confirm the degradation of HSP90 client protein of EGFR, Her2, Met, Akt, c-Raf, Cpk4 and most of the client proteins were denatured at 500 nM.

II. Synthesis of Benzamide Compounds and Evaluation of Biological Activity

REFERENCE EXAMPLE 2

Reagents and Experimental Apparatus

The reagents purchased from Sigma-Aldrich (St. Louis, Mo., USA), acros organics (Thermo Fisher Scientific In., Gell, Belgium), alfa aesar (A Johnson Malley Company, Karlsruhe, Germany) and Daejung (Daejeonghwageum Co., Kyunggi-do, Korea) were used. Compound synthesis was carried out under argon or in atmosphere, and in some cases microwave (Biotage®, Uppsala, Sweden) was used. Extraction, recrystallization, column chromatography and MPLC (medium pressure liquid column chromatography) were used to purify the product after synthesis. Silica gel 60 (0.040-0.063 mm) was used as a filler for the column chromatography and SNAP cartridge (KP-Sil 25 g or KP-C18-HS 30 g) was used for MPLC.

Structure of each compound was identified using $^1$H NMR and $^{13}$C NMR spectra by a Bruker spectrospin 400 spectrometer (Bruker co., Billerica, Mass., USA). CDCl$_3$, CD$_3$OD or dimethyl sulfoxide (DMSO)-d$_6$ was used as a solvent and the chemical shift value (δ) was expressed in ppm and the peaks were expressed in d (doublet), t (triplet), m (multiplet) and dd (doublet of doublet).

A power supply unit (BioRad co., Hercules, Calif.), an image analyzer (Fuji, Tokyo, Japan) and a microplate reader (TECAN, Mannedorf, Switerland) were used for evaluating the biological activity.

EXAMPLE 3

Synthesis of Benzamide-Based Compound

Compounds 6a to 6h and 8a to 8c were synthesized in the same manner as in Reaction Scheme 4 below.

[Reaction Scheme 4]

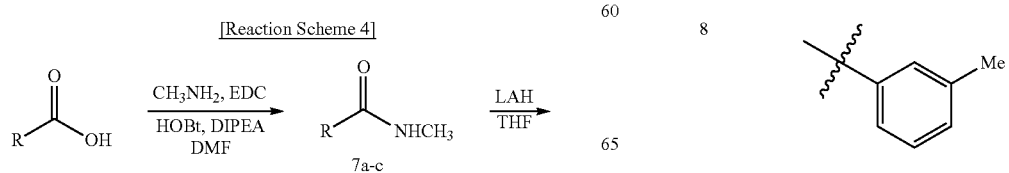

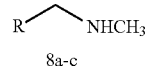

| entry | R | compound |
|---|---|---|
| 1 | phenyl | 6a |
| 2 | 4-OMe phenyl | 6b |
| 3 | 3,4-di-OMe phenyl | 6c |
| 4 | benzo[1,3]dioxole | 6d |
| 5 | 3,4,5-tri-OMe phenyl | 6e |
| 6 | 2-Cl-3,4,5-tri-OMe phenyl | 6f |
| 7 | 2-Br-3,4,5-tri-OMe phenyl | 6g |
| 8 | 3-Me phenyl | 6h |

| entry | R | compound |
|---|---|---|
| 9 | *-o-tolyl (Me ortho)* | 7a, 8a |
| 10 | *-p-tolyl (Me para)* | 7b, 8b |
| 11 | *-C6H4-C(O)OMe (para)* | 7c, 8c |

1. Amine Synthesis Method I (6a-h)

One equivalent of each aldehyde and 1.5 equivalents of 40% methylamine in distilled water (d-water) were dissolved in MeOH and stirred at room temperature for 30 minutes. 0.5 equivalent of sodium borohydride ($NaBH_4$) was slowly added at 0° C. and then stirred for 1 hour. Thereafter, $H_2O$ was added to the mixture, MeOH was removed by distillation under reduced pressure, and extracted three times with dichloromethane (DCM). The DCM layer was dried with $NaSO_4$ and filtered and the solvent was removed by distillation under reduced pressure to obtain 6a-h in yields of 32.0-76.4%.

2. Amine Synthesis Method II (8a-c)

One equivalent of benzoic acid, 1.5 equivalents 40% of methylamine in d-water, 2 equivalents of EDC (1-ethyl-3-(3-dimethylaminopropyl) carbodiimide) or DCC N,N-equivalent dicyclohexylcarbodiimide), 1 equivalent of HOBt (hydroxybenzotriazole) and 1 equivalent of DIPEA (NN-diiso-propylethylamine) were dissolved in dimethylformamide (DMF) and microwave-reacted at 120° C. and 20 bar for 3 hours. After dissolving in ethyl acetate (EA) and washing several times with 1N HCl saturated aqueous solution, the EA layer was dried with $Na_2SO_4$ and filtered, and the solvent was removed by distillation under reduced pressure. After purification by MINX or column chromatography, 1 equivalent of the purified compound was dissolved in tetrahydrofuran (THF), 3 equivalents of lithium aluminum hydride (LAH) was slowly added at 0° C. and stirred for 12 hours. The reaction was quenched with a saturated aqueous solution of 10% NaOH and $H_2O$ and extracted with ether. The ether layer was dried with $Na_2SO_4$ and filtered, and the solvent was removed by distillation under reduced pressure. After purification by column chromatography. 8a-c was obtained in yields of 22.5% and 88.7%.

Compounds 14a to 14i were synthesized in the same manner as in Reaction Scheme 5 below.

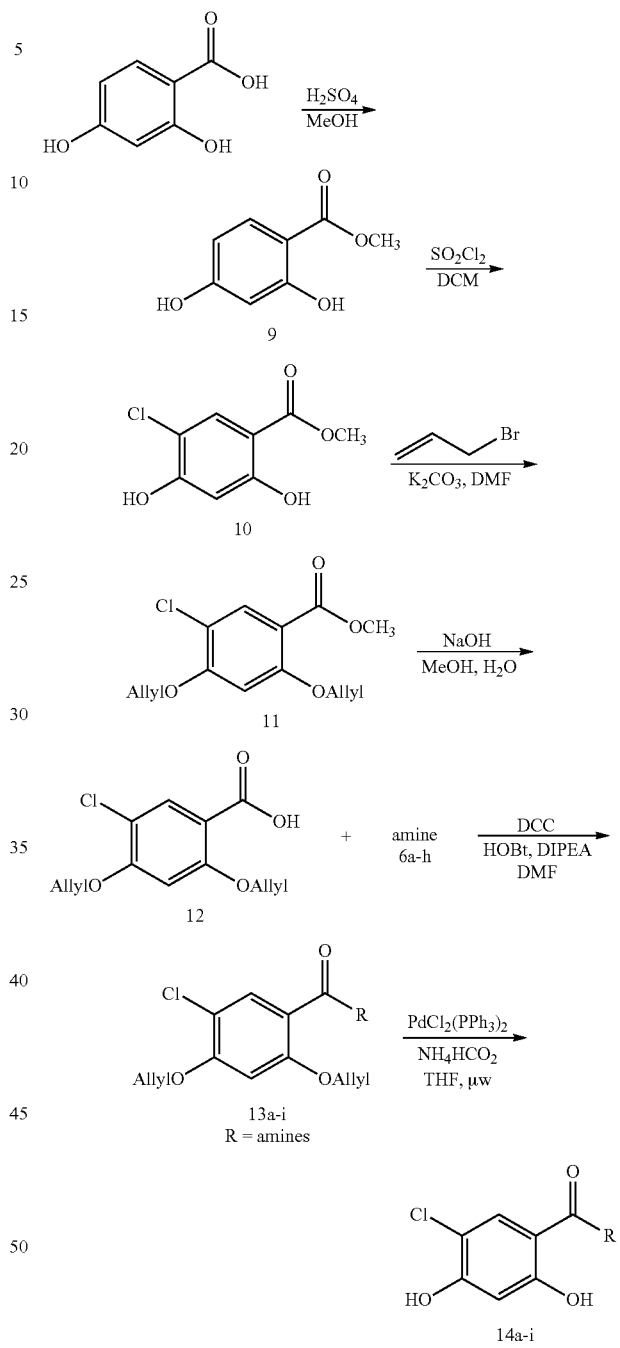

[Reaction Scheme 5]

| entry | R | compound |
|---|---|---|
| 1 | *-NH-CH2-C6H5* | 14a |

| entry | R | compound |
|---|---|---|
| 2 | -N(Me)-CH2-C6H5 | 14b |
| 3 | -N(Me)-CH2-C6H4-OMe (4-OMe) | 14c |
| 4 | -N(Me)-CH2-C6H3(OMe)2 (3,4-diOMe) | 14d |
| 5 | -N(Me)-CH2-(3,4-methylenedioxyphenyl) | 14e |
| 6 | -N(Me)-CH2-C6H2(OMe)3 (3,4,5-triOMe) | 14f |
| 7 | -N(Me)-CH2-C6H(Cl)(OMe)3 | 14g |
| 8 | -N(Me)-CH2-C6H(Br)(OMe)3 | 14h |
| 9 | -N(Me)-CH2-C6H4-Me (3-Me) | 14i |

3. Methyl 2,4-dihydroxybenzoate (9)

2,4-dihydroxybenzoic acid (10.00 g, 64.88 mmol) and sulfuric acid ($H_2SO_4$) of 5 mL were added to 40 mL of MeOH and refluxed at 100° C. for 24 hours. After cooling at room temperature, the solvent was removed by distillation under reduced pressure, and $H_2O$ was added at 0° C. The resulting white solid was dissolved in EA and washed with a saturated aqueous $NaHCO_3$ solution. The EA layer was dried with $Na_2SO_4$ and filtered, and the solvent was removed by distillation under reduced pressure to obtain Compound 9 in a yield of 85%.

$^1$H NMR (400 MHz, $CDCl_3$) d 11.0 (s, 1H), 7.73 (d, J=8.4 Hz, 1H), 6.41-6.37 (m, 2H), 5.78 (s, 1H), 3.92 (s, 3H).

4. Methyl 5-chloro-2,4-dihydroxybenzoate (10)

Compound 8 (8.30 g, 49.41 mmol) and sulfuryl chloride ($SO_2Cl_2$) (4.11 mL, 56.83 mmol) were added to DCM and stirred at room temperature for 24 hours. The solvent was removed by distillation under reduced pressure, dissolved in EA, washed with a saturated aqueous $NaHCO_3$ solution, dried over $Na_2SO_4$ and filtered, and the solvent was removed by distillation under reduced pressure. It was purified by column chromatography using a solvent mixture of EA:hexane=1:9 to obtain Compound 10 in a yield of 32.5%.

$^1$H NMR (400 MHz, $CDCl_3$) d 10.8 (s, 1H), 7.82 (s, 1H), 6.61 (s, 1H), 5.91

5. Methyl 2,4-bis (allyloxy)-5-chlorobenzoate (11)

Compound 9 (1.10 g, 5.46 mmol), allyl bromide (1.23 mL, 14.20 mmol) and $K_2CO_3$ (1.96 g, 14.20 mmol) were dissolved in DMF. It was stirred under argon at room temp me for 12 hours, then dissolved in EA and washed with a saturated aqueous $NaHCO_3$ solution. The EA layer was dried over $Na_2SO_4$, and the solvent was removed by distillation under reduced pressure to obtain Compound 11 in a yield of 83%.

$^1$H NMR (400 MHz, $CDCl_3$) d 7.85 (s, 1H), 7.25 (s, 1H), 6.44-5.95 (m, 2H), 5.50-5.40 (m, 2H), 5.30-5.26 (m, 2H), 4.58-4.45 (m, 4H), 3.81 (s, 3H).

6. 2,4-bis(allyloxy)-5-chlorobenzoic Acid (12)

Compound 8 (1.27 g, 5.64 mmol) and NaOH (1.12 g, 28.1 mmol) were added to $H_2O$ (20 mL) and MeOH (20 mL) and stirred at room temperature for 8 hours, and then was dissolved in EA and washed with 3N HCl. The EA layer was dried over $Na_2SO_4$ and then the solvent was removed by distillation under reduced pressure to obtain Compound 12 in a yield of 74%.

$^1$H NMR (400 MHz, $CDCl_3$) d 8.16 (s, 1H), 6.54 (s, 1H), 6.10-5.99 (m, 2H), 5.51-5.35 (m, 2H), 4.76-4.65 (m, 4H).

7. N-Benzyl-5-chloro-2,4-dihydroxybenzamide (14a)

Compound 12 (0.50 g, L86 mmol), benzylamine (0.26 g, 1.86 mmol), HOBt (0.25 g, 1.86 mmol), DCC (0.77 g, 3.72 mmol) and DIPEA (0.32 mL, 1.86 mmol) were dissolved in DMF and microwave reaction was performed at 80° C. and 20 bar for 3 hours. DMF was removed by distillation under reduced pressure and Compound 13a was obtained by purifying by MPLC ($R_f$=0.19, EA:hexane 1:4). Compound 13a vas dissolved in THF, and $PdCl_2(PPh_3)_2$ (20 mg) and $NH_4HCO_2$ (200 mg) were added thereto, followed by microwave reaction at 120° C. and 20 bar for 30 minutes.

It was dissolved in EA, washed with $H_2O$, and the EA layer was dried with $Na_2SO_4$ followed by filtering. The solvent was removed by distillation under reduced pressure, and Compound 14a was obtained purifying by MPLC ($R_f$=0.13, EA:hexane=3:7) in yield of 53.2%.

$^1$H NMR (400 MHz, MeOD) d 7.77 (s, 1H), 7.29-7.26 (m, 4H), 7.22-7.19 (m, 1H), 6.40 (s, 1H), 4.50 (s, 2H). $^{13}$C NMR (100 MHz, MeOD) d 165.2, 157.0, 154.2, 135.3, 125.2, 124.7, 123.7, 123.4, 108.1, 104.9, 100.2, 39.1.

8. N-Benzyl-5-chloro-2,4-dihydroxy-n-methylbenzamide (14b)

Compound 12 (0.30 g, 1.12 mmol), Compound 6a (0.21 g, 1.67 mmol), HOBt (0.15 g, 1.12 mmol), DCC (0.46 g, 2.23 mmol) and DIPEA (0.19 mL, 1.12 mmol) were dissolved in DMF and microwave reaction was performed at 80° C. and 20 bar for 3 hours. It was then dissolved in EA and washed with $H_2O$, and the EA layer was dried with $NaSO_4$ and filtered, and then the solvent was removed by distillation under reduced pressure, it was purified by MPLC ($R_f$=0.31, EA:hexane=3:7) to obtain Compound 13b. Compound 13b was dissolved in THF, and $PdCl_2(PPh_3)_2$ (20 mg) and $NH_4HCO_2$ (200 mg) were added thereto, followed by microwave reaction at 120° C. and 20 bar for 30 minutes. After dissolving in EA and washing with $H_2O$, the EA layer was dried with $Na_2SO_4$ and filtered, and the solvent was removed by distillation under reduced pressure. Compound 14b was obtained by purifying by MPLC ($R_f$=0.28, EA:hexane=2:3) at a yield of 62.5%.

$^1H$ NMR (400 MHz, MeOD) d 7.35-7.24 (m, 5H), 7.16 (s, 1H), 6.50 (s, 1H), 2.89 (s, 3H).

9. 5-chloro-2,4-dihydroxy-n-(4-methoxybenzyl)-n-methylbenzamide (14c)

Compound 12 (0.30 g, 1.12 mmol), Compound 6b (0.18 g, 1.67 mmol), HOBt (0.15 g, 1.12 mmol), DCC (0.46 g, 2.23 mmol) and DIPEA (0.19 mL, 1.12 mmol) were dissolved in DMF and microwave reaction was performed at 80° C. and 20 bar for 3 hours. DMF was removed by distillation under reduced pressure, and Compound was obtained by purifying by MPLC ($R_f$=0.20, EA:hexane=3:7). Compound 13c was dissolved in THF, and $PdCl_2(PPh_3)_2$ (20 mg) and $NH_4HCO_2$ (200 mg) were added thereto, followed by microwave reaction at 120° C. and 20 bar for 30 minutes. After dissolving in EA and washing with $H_2O$, the EA layer was dried with $Na_2SO_4$ and filtered, and the solvent was removed by distillation under reduced pressure.

Compound 14c was obtained by purifying by MPLC ($R_f$=0.30, EA:hexane=2: 3) in a yield of 63.8%.

$^1H$ NMR (400 MHz, $CDCl_3$) d 7.27 (s, 1H), 7.20 (d, J=8.4 Hz, 2H), 6.90 (d, J=6.8 Hz, 2H), 6.62 (s, 1H), 4.64 (s, 2H), 3.80 (s, 3H), 3.03 (s, 3H). $^{13}C$ NMR (100 MHz, $CDCl_3$) d 171.1, 159.6, 159.3, 155.2, 129.0, 128.8, 128.0, 114.4, 111.1, 110.5, 105.2, 55.4.

10. 5-chloro-n-(3,4-dimethoxybenzyl)-2,4-dihydroxy-n-methylbenzamide (14d)

Compound 12 (0.33 g, 1.23 mmol) Compound 6c (0.33 g, 1.84 mmol), HOBt (0.17 g, 1.23 mmol), DCC (0.51 g, 2.46 mmol) and DIPEA (0.22 mL, 1.23 mmol) were dissolved in DMF and microwave reaction was performed at 120° C. and 20 bar for 3 hours. Compound 13d was obtained by purifying by MPLC ($R_f$=0.26, EA:hexane=2:3). Compound 13d was dissolved in THF, and $PdCl_2(PPh_3)_2$ (20 mg) and $NH_4HCO_2$ (200 mg) were added thereto, followed by microwave reaction at 120° C. and 20 bar for 30 minutes. After dissolving in EA and washing with $H_2O$, the EA layer was dried with $Na_2SO_4$ and filtered, and the solvent was removed by distillation under reduced pressure. Compound 14d was obtained by purifying by MPLC ($R_f$=0.22, EA:hexane=1:1) in a yield of 63.8%.

$^1H$ NMR (400 MHz, $CDCl_3$) d 7.31 (s, 1H), 6.88-6.81 (m, 3H), 6.66 (s, 1H), 4.65 (s, 2H), 3.88 (d, J=6.4 Hz, 6H), 3.07 (s, 3H). $^{13}C$ NMR (100 MHz, $CDCl_3$) d 170.5, 155.3, 149.1, 148.3, 131.9, 131.8, 128.8, 128.7, 128.6, 128.5, 119.3, 111.0, 110.5, 105.1, 55.7.

11. N-(benzo[d][1,3]dioxol-5-ylmethyl)-5-chloro-2, 4-dihydroxy-n-methylbenzamide (14e)

Compound 12 (0.30 g, 1.12 mmol), Compound 6d (0.28 g, 1.67 mmol), HOBt (0.15 g, 1.12 mmol), DCC (0.46 g, 2.23 mmol) and DIPEA (0.19 mL, 1.12 mmol) were in DMF and microwave reaction vas performed at 80° C. and 20 bar for 3 hours. DMF was removed by distillation under reduced pressure and then Compound 13e was obtained by purifying by MPLC ($R_f$=0.25, EA:hexane=3:7). Compound 13e was dissolved in Tiff, and $PdCl_2(PPh_3)_2$ (20 mg) and $NH_4HCO_2$ (200 mg) were added thereto, and microwave reaction was performed at 120° C. and 20 bar for 30 minutes. After dissolving in EA and washing with $H_2O$, the EA layer was dried with $Na_2SO_4$ and filtered, and the solvent was removed by distillation under reduced pressure and Compound 14e was obtained by purifying by MPLC ($R_f$=0.23, EA:hexane=2.3) in a yield of 78.6%.

$^1H$ NMR (400 MHz, $CDCl_3$) d 7.28 (s, 1H), 6.79-6.72 (m, 3H), 6.60 (s, 1H), 5.96 (s, 2H), 4.59 (s, 2H), 3.03 (s, 3H). $^{13}C$ NMR (100 MHz, $CDCl_3$) d

12. 5-chloro-2,4-dihydroxy-n-methyl-n-(3,4,5-trimethoxybenzyl) benzamide (14f)

Compound 1.2 (0.30 g, 1.12 mmol), Compound 6e (0.35 g, 1.23 mmol), (0.15 g, 1.12 mmol), DCC (0.46 g, 2.23 mmol) and DIPEA (0.19 mL, 1.12 mmol) were dissolved in DMF and microwave reaction was performed at 80° C. and 20 bar for 3 hours. Compound 13f was obtained by purifying by MPLC ($R_f$=0.20, EA:hexane=2:3). Compound 13f vas dissolved in THF and $PdCl_2(PPh_3)_2$ (20 mg) and $NH_4HCO_2$ (200 mg) were added thereto, followed by microwave reaction at 120° C. and 20 bar for 30 minutes. After dissolving in EA and washing with $H_2O$, the EA layer was dried with $Na_2SO_4$ and filtered, and the solvent was removed by distillation under reduced pressure and Compound 14f was obtained by purifying by MPLC ($R_f$=0.26, EA:hexane=3:2) in yield of 67.0%.

$^1H$ NMR (400 MHz, $CDCl_3$) d 7.23 (s, 1H), 6.56 (s, 1H), 6.47 (s, 1H), 4.59 (s, 2H), 3.80 (d, J=1.2 Hz, 9H), 3.02 (s, 3H). $^{13}C$ NMR (100 MHz, $CDCl_3$) d 171.2, 158.7, 155.4, 153.6, 137.3, 132.0, 128.8, 111.6, 110.8, 105.1, 104.5, 61.0, 56.2.

13. 5-chloro-n-(2-chloro-3,4,5-trimethoxybenzyl)-2, 4-dihydroxy-n-methylbenzamide (14 g)

Compound 12 (0.20 g, 0.74 mmol), Compound 6f (0.27 g, 1.12 mmol), HOBt (0.10 g, 0.74 mmol), DCC (0.31 g, 1.49 mmol) and DIPEA (0.15 mL, 0.74 mmol) were dissolved in DMF and microwave reaction was performed at 120° C. and 20 bar for 3 hours. After washing with EA and washing with $H_2O$, the EA layer was dried with $NaSO_4$, filtered, and the solvent was removed by distillation under reduced pressure and Compound 13g was obtained by purifying by MPLC ($R_f$=0.26, EA:hexane=3:7). Compound 13g was dissolved in THF, $PdCl_2(PPh_3)_2$ (20 mg) and $NH_4HCO_2$ (200 mg) were added and microwave reaction was performed at 120° C. and 20 bar for 30 minutes, was dried over Na$_2$SO$_4$ and filtered, and the solvent was removed by distillation under reduced pressure. Compound 14g was obtained by purifying by MPLC (R$_f$=0.20, EA:hexane=1:1) in a yield of 41.9%.

$^1$H NMR (400 MHz, CDCl$_3$) d 7.21 (s, 1H), 6.75 (s, 1H), 6.47 (s, 1H), 4.75 (s 2H), 3.90 (d, J=9.2 Hz, 6H), 3.83 (s, 3H), 3.03 (s, 3H). $^{13}$C NMR (100 MHz, CDCl$_3$) d 171.1, 156.3, 155.4, 152.5, 150.0, 142.4, 132.0, 129.3, 128.9, 119.2, 113.0, 111.3, 107.0, 104.2, 61.2, 56.1, 49.8.

14. N-(2-bromo-3,4,5-trimethoxybenzyl)-5-chloro-2,4-dihydroxy-n-methylbenzamide (14h)

Compound 12 (019 g, 0.69 mmol), Compound 6 g (0.30 g, 1.03 mmol), HOBt (0.09 g, 0.69 mmol) DCC (028 g. 1.38 mmol) and DIPEA (0.12 mL, 0.69 mmol) was dissolved in DMF and microwave reaction was performed at 120° C. and 20 bar for 3 hours. After dissolving in EA and washing with H$_2$O, the EA layer was dried with Na$_2$SO$_4$ and filtered, and the solvent was removed by distillation under reduced pressure. Compound 13h was obtained by purifying by MPLC (R$_f$=0.24, EA:hexane 3:7).

Compound 13h was dissolved in THF, and PdCl$_2$(PdCl$_2$(PPh$_3$)$_2$ (20 mg) and NH$_4$HCO$_2$ (200 mg) were added thereto, followed by microwave reaction at 120° C. and 20 bar for 30 minutes. After dissolving in EA and washing with H$_2$O, the EA layer was dried with Na$_2$SO$_4$ and filtered, and the solvent was removed by distillation under reduced pressure. Compound 14h was obtained by purifying by MPLC (R$_f$=24, EA:hexane=1:1) in yield of 20.5%.

$^1$H NMR (400 MHz, CDCl$_3$) d 7.15 (s, 1H), 6.69 (s, 1H), 6.42 (s, 1H), 4.68 (s, 2H), 3.83 (d, J=6.0 Hz, 6H), 3.77 (d, 3H), 2.98 (s, 3H). $^{13}$C NMR (100 MHz, CDCl$_3$) d 160.8, 155.2, 153.4, 151.4, 143.0, 130.9, 128.6, 110.7, 110.3, 105.4, 61.4, 61.3, 60.7, 56.5.

15. 5-chloro-2,4-dihydroxy-n-methyl-n-(3-methyl-benzyl)benzamide (14i)

Compound 12 (0.25 g, 0.93 mmol), Compound 6h (0.19 g, 1.40 mmol), HOBt (0.13 g, 0.93 mmol), DCC (0.39 g, 1.86 mmol) and DIPEA (0.17 mL, 0.93 mmol) were in DMF and microwave reaction was performed at 120° C. and 20 bar for 3 hours. After dissolving in EA and washing with H$_2$O, the EA layer was dried with Na$_2$SO$_4$ and filtered, and the solvent was removed by distillation under reduced pressure and Compound 13i was obtained by purifying by MPLC (R$_f$=0.22, EA:hexane=1:4).

Compound 13i was dissolved in THF, and PdCl$_2$(PPb$_3$)$_2$ (20 mg) and NH$_4$HCO$_2$ (200 mg) were added thereto, and microwave reaction was performed at 120° C. and 20 bar for 30 minutes. After dissolving in EA and washing with H$_2$O, the EA layer was dried with Na$_2$SO$_4$ and filtered, and the solvent was removed by distillation under reduced pressure and Compound 14i was obtained by purifying by MPLC (R$_f$=0.20, EA:hexane=3:7) in a yield of 68.7%.

$^1$H NMR (400 MHz, CDCl$_3$) d 7.31 (s, 1H), 7.28 (d, J=7.6 Hz, 1H), 7.15 (d, J=7.6 Hz, 1H), 7.10-7.09 (m, 2H), 6.65 (s, 1H), 4.70 (s, 2H), 3.08 (s, 3H), 2.38 (s, 3H). $^{13}$C NMR (100 MHz, CDCl$_3$) d 171.3, 160.0, 155.2, 138.8, 136.0, 128.9, 128.8, 128.7, 128.3, 124.6, 110.9, 110.4, 105.2, 36.8.

Compounds 16a and 16b were synthesized in the same manner as in Reaction Scheme 6 below.

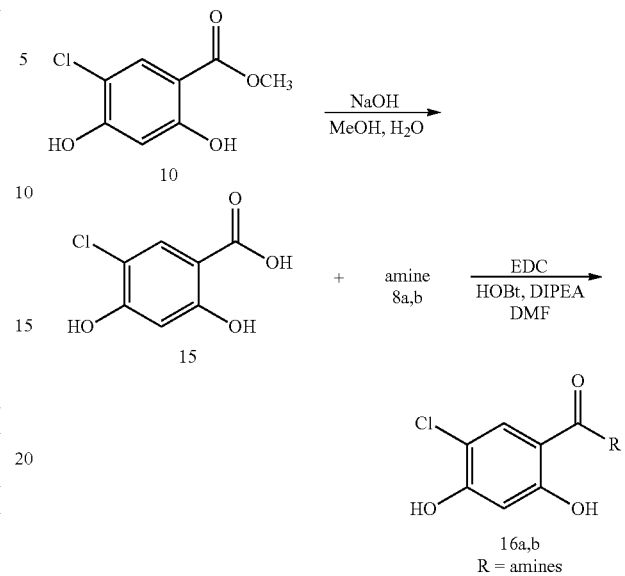

[Reaction Scheme 6]

| entry | R | compound |
|---|---|---|
| 10 | N-CH$_2$-(2-methylphenyl), N-Me | 16a |
| 11 | N-CH$_2$-(4-methylphenyl), N-Me | 16b |

16. 5-chloro-2,4-dihydroxybenzoic Acid (15)

Compound 9 (1.98 g, 9.77 mmol) and NaOH (1.95 g, 48.80 mmol) were added to H$_2$O (30 mL) and MeOH (30 mL) and stirred at room temperature for 12 hours. It was dissolved in EA, washed with 3N HCl saturated aqueous solution, and the EA layer was dried with Na$_2$SO$_4$ and filtered. The solvent was removed by distillation under reduced pressure to obtain Compound 15 in a yield of 100% by purifying by MPLC.

$^1$H NMR (400 MHz, CDCl$_3$) d 7.76 (s, 1H), 6.41 (s, 1H).

17. 5-chloro-2,4-dihydroxy-n-methyl-n-(2-methyl-benzyl)benzamide (16a)

Compound 15 (0.17 g, 0.92 mmol), Compound 8a (0.19 g, 1.40 mmol), HOBt (0.12 g, 0.92 mmol), EDC (0.35 g, 1.86 mmol) and DIPEA (0.16 mL, 0.92 mmol) were dissolved in DMF and microwave reaction was performed at 120° C. and 20 bar for 3 hours. It was dissolved in EA, washed with a saturated aqueous solution of 1N HCl, dried over Na$_2$SO$_4$ and filtered. The solvent was removed by distillation under reduced pressure to obtain Compound 16a in a. The residue was purified by MPLC ($R_f$=0.23, EA:hexane=1:4) to obtain Compound 16a in a yield of 90.5%.

$^1$H NMR (400 MHz, CDCl$_3$) d 7.25-7.24 (m, 4H), 6.65 (s, 1H), 4.72 (s, 2H), 3.07 (s, 3H), 2.27 (s, 3H). $^{13}$C NMR (100 MHz, CDCl$_3$) d 160.9, 155.2, 136.4, 134.0, 131.0, 128.7, 128.0, 127.4, 126.7, 110.7, 110.2, 105.3, 19.2.

18. 5-chloro-2,4-dihydroxy-n-methyl-n-(4-methyl-benzyl)benzamide (16b)

Compound 15 (0.21 g, 1.12 mmol), Compound 8b (0.23 g, 1.69 mmol), HOBt (0.15 g, 1.12 mmol), EDC (0.43 g, 2.25 mmol) and DIPEA (0.20 mL, 1.12 mmol) were dissolved in DMF Microwave reaction was performed at 120° C. and 20 bar for 3 hours. It was dissolved in EA, washed with 3N HCl saturated aqueous solution, and then the EA layer was dried with Na$_2$SO$_4$, filtered. The solvent was removed by distillation under reduced pressure to obtain Compound 16b in a yield of 26.0% by purifying by MPLC ($R_f$=0.23, EA:hexane=1:4).

$^1$H NMR (400 MHz, CDCl$_3$) d 7.28 (s, 1H), 7.17 (t, J=9.2 Hz, 9.2 Hz, 4H), 6.63 (s, 1H), 4.67 (s, 2H), 3.04 (s, 3H), 2.35 (s, 3H). $^{13}$C NMR (100 MHz, CDCl$_3$) d 160.1, 155.0, 137.7, 133.0, 129.7, 128.6, 128.5, 127.6, 127.3, 110.9, 110.2, 105.2, 21.2.

Compounds 21a to 21f were synthesized in the same manner as in Reaction Scheme 7 below.

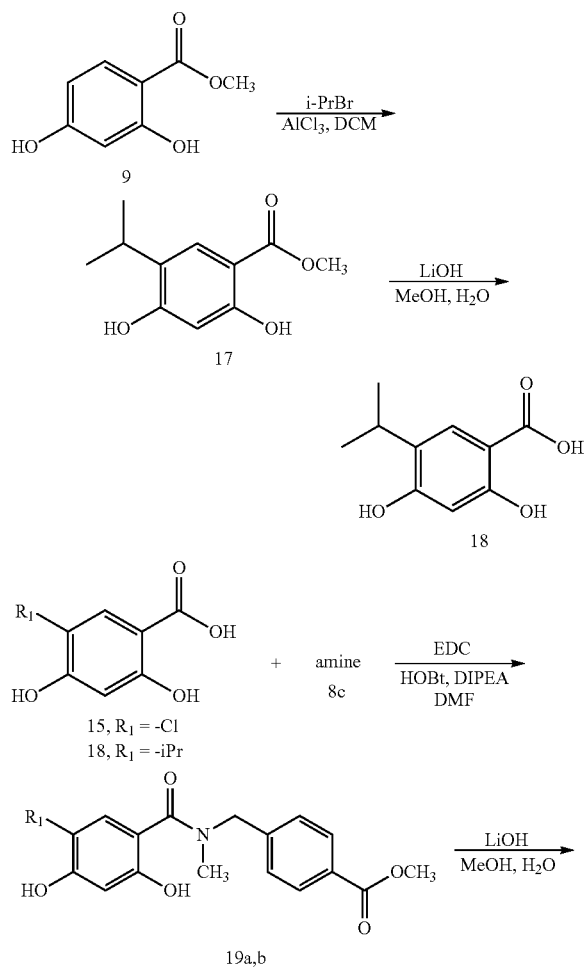

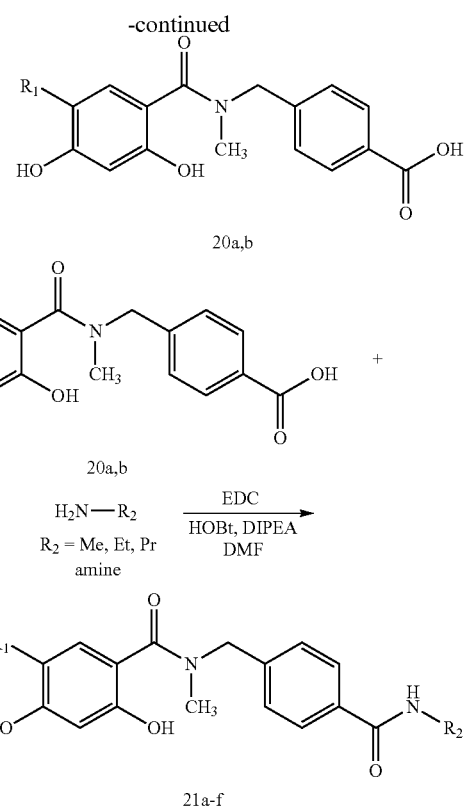

19. Methyl 2,4-dihydroxy-5-isopropylbenzoate (17)

Compound 9 (10.70 g, 63.50 mmol), AlCl$_3$ (16.90 g, 127.0 mmol) and 2-bromopropane (11.90 mL, 127.0 mmol) were dissolved in DCM (125 mL) and refluxed at 50° C. for 24 hours under argon injection. 2 equivalents of AlCl$_3$ and 2-bromopropane were added, respectively in a 6-hour period. The reaction mixture was adjusted to pH 6 with a saturated aqueous solution of 10% NaOH and the solvent was removed by distillation under reduced pressure, and the residue was dissolved in EA and washed with a saturated aqueous NaHCO$_3$ solution. The EA layer was dried with Na$_2$SO$_4$, filtered and the solvent was removed by distillation under reduced pressure. Compound 17 was obtained by purifying by column chromatography using a solvent mixed in EA:hexane=1:9, in a yield of 34.5%.

$^1$H NMR (400 MHz, CDCl$_3$) d 12.61 (s, 1H), 7.52 (s, 1H), 6.35 (s, 1H), 6.31 (s, 1H), 3.22-3.12 (m, 1H), 2.61 (s, 3H), 1.27 (d, J=6.8 Hz, 6H). $^{13}$C NMR (100 MHz, CDCl$_3$) d 170.7, 161.6, 159.6, 128.1, 127.1, 105.7, 103.2, 52.2, 26.7, 22.8.

20. 2,4-dihydroxy-5-isopropylbenzoic Acid (18)

Compound 17 (4.60 g, 21.90 mmol) and LiOH (10 g) were added into H$_2$O (30 mL) and MeOH (30 mL) at 70° C. and refluxed for 12 hours. It was dissolved in EA and washed with 3N HCl saturated aqueous solution. The EA layer was dried with Na$_2$SO$_4$, filtered and the solvent was removed by distillation under educed pressure to obtain Compound 18 in a yield of 60.5%.

$^1$H NMR (400 MHz, CDCl$_3$) d 7.68 (s, 1H), 6.30 (s, 1H), 3.19-3.12 (m, 1H), 1.17 (d, J=4.0 Hz, 6H).

21. Methyl 4-((5-chloro-2,4-dihydroxy-n-methyl-benzamido)methyl) benzoate (19a) and Methyl 4-((2,4-Dihydroxy-5-Isopropyl-N-Methylbenzamido)Methyl)Benzoate (19b)

1 equivalent of Compound 12 or 18, 1.5 equivalents of Compound 8c, 1 equivalent of HOBt, 2 equivalents of EDC and 1 equivalent of DIPEA were dissolved in DMF and microwave reaction was performed at 120° C. and 20 bar for 3 hours. After dissolving in EA and washing with $H_2O$, the EA layer was dried with $NaSO_4$, filtered, and then the solvent was removed by distillation under reduced pressure. Compound 19a or 19b was obtained by purifying by MPLC according to the conditions of each compound in yields of 76.1%, 81.7%, respectively.

19a: $^1$H NMR (500 MHz, $CDCl_3$) d 8.03 (d, J=6.6 Hz, 2H), 7.35 (d, J=6.6 Hz, 2H), 7.25 (s, 1H), 6.62 (s, 1H), 4.75 (s, 2H), 3.91 (s, 3H), 3.07 (s, 3H).

19b: $^1$H NMR (500 MHz, $CDCl_3$) d 8.05 (d, J=6.7 Hz, 2H), 7.37 (d, J=6.7 Hz, 2H), 7.11 (s, 1H), 6.42 (s, 1H), 4.76 (s, 2H), 3.92 (s, 3H), 3.13-3.04 (m, 1H), 3.05 (s, 3H), 0.94 (d, J=5.3 Hz, 6H).

22. 4-((5-chloro-2,4-dihydroxy-n-methylbenzamido)methyl)benzoic Acid (20a) and 4-((2,4-dihydroxy-5-isopropyl-n-methylbenzamido)methyl)benzoic Acid (20b)

1 equivalent of Compound 19a or 19b and LiOH (2.0 g) were added to $H_2O$ (20 mL) and MeOH (20 mL) and stirred at room temperature for 3 hours. It was dissolved in EA and washed with 3N HCl saturated aqueous solution. The EA layer was dried with $Na_2SO_4$ and filtered, and the solvent was removed by distillation under reduced pressure to obtain Compounds 20a and 20b at a yield of 84.8% and 88.1%, respectively.

20a: $^1$H NMR (500 MHz, $CDCl_3$) d 8.13 (d, J=6.66 Hz, 2H), 7.41 (d, J=6.6 Hz, 2H), 7.30 (s, 1H), 6.68 (s, 1H), 4.79 (s, 2H), 3.12 (s, 3H).

20b: $^1$H NMR (500 MHz, MeOD) d 8.00 (d, J=6.5 Hz, 2H), 7.41 (d, J=5.8 Hz, 2H), 7.0 (s, 1H), 6.34 (s, 1H), 4.86 (s, 2H), 3.18-3.11 (m, 1H), 3.0 (s, 3H), 1.11 (d, J=5.2 Hz, 6H).

23. 5-chloro-2,4-dihydroxy-n-methyl-n-(4-(methylcarbamoyl)benzyl) benzamide (21a)

Compound 20a (0.27 g, 0.79 mmol), 40% methylamine in d-water (0.10 mL, 1.18 mmol), HOBt (0.11 g, 0.79 mmol), EDC (0.30 g, 1.58 mmol) and DIPEA (0.14 mL, 0.79 mmol) was dissolved in DMF and microwave reaction was performed at 120° C. and 20 bar for 2 hours. It was dissolved in EA, washed with a saturated aqueous solution of 1N HCl, dried over $Na_2SO_4$ and filtered, and the solvent was removed by distillation under reduced pressure. Compound 21a was obtained by purifying by MPLC (C18 column, $R_f$=0.21, $H_2O$:MeOH=4:1) in a yield of 16.7%.

$^1$H NMR (500 MHz, $CDCl_3$) d 7.78 (d, J=6.6 Hz, 2H), 7.36 (d, J=6.6 Hz, 2H), 7.30 (s, 1H), 6.68 (s, 1H), 4.75 (s, 2H), 3.09 (s, 3H), 3.03 (d, J=3.8 Hz, 3H).

24. 5-chloro-n-(4-(ethylcarbamoyl)benzyl)-2,4-dihydroxy-n-methylbenzamide (21b)

Compound 20a (0.27 g, 0.79 mmol), 70% ethylamine in $H_2O$ (0.10 mL, 1.18 mmol), HOBt (0.11 g, 0.79 mmol), EDC (0.30 g, 1.58 mmol) mL, 0.79 mmol) were dissolved in DMF and microwave reaction was performed at 120° C. and 20 bar for 2 hours. After dissolving in EA and washing with IN HCl saturated aqueous solution, the EA layer is dried with $Na_2SO_4$ and filtered, and the solvent is removed by distillation under reduced pressure. Compound 21b was obtained by purifying by MPLC (C18 column, $R_f$=0.21, $H_2O$:MeOH=4:1) in a yield of 31.2%.

$^1$H NMR (500 MHz, $CDCl_3$) d 7.78 (d, J=6.6 Hz, 2H), 7.35 (d, J=6.6 Hz, 2H), 7.30 (s, 1H), 6.67 (s, 1H), 4.75 (s, 2H), 3.54-3.49 (m, 2H), 2.96 (s, 3H), 1.26 (t, J=5.8 Hz, 5.8 Hz, 3H). $^{13}$C NMR (100 MHz, $CDCl_3$) d

25. 5-chloro-2,4-dihydroxy-n-methyl-n-(4-(propylcarbamoyl)benzyl)benzamide (21c)

Compound 20a (0.26 g, 0.76 mmol), propylamine (0.10 mL, 1.14 mmol), HOBt (0.10 g, 0.76 mmol), EDC (0.30 g, 1.52 mmol) and DIPEA (0.10 mL, 0.76 mmol) were dissolved in DMF and microwave reaction was performed at 120° C. and 20 bar for 3 hours. After dissolving in EA and washing with 1N HCl saturated aqueous solution, the EA layer was dried with $NaSO_4$, filtered and the solvent was removed by distillation under reduced pressure. Compound 21c was obtained by purifying by MPLC (C18 column, $R_f$=0.21, $H_2O$:MeOH=7:3) in a yield of 45.5%.

$^1$H NMR (500 MHz, $CDCl_3$) d 7.78 (d, J=6.6 Hz, 2H), 7.35 (d, J=6.6 Hz, 2H), 7.28 (s, 1H), 6.67 (s, 1H), 4.75 (s, 2H), 3.46-3.42 (m, 2H), 3.09 (s, 3H), 1.67-1.62 (m, 2H), 1.00 (t, J=5.9 Hz, 5.9 Hz, H).

26. 2,4-dihydroxy-5-isopropyl-n-methyl-n-(4-(methylcarbamoyl)benzyl) benzamide (21d)

Compound 20b (0.21 g, 0.62 mmol), 40% methylamine in d-water (0.08 mL, 0.93 mmol), HOBt (0.08 g, 0.62 mmol), EDC (0.23 g, 1.24 mmol) and DIPEA (0.11 mL, 0.62 mmol) were dissolved in DMF, and microwave reaction was performed at 120° C. and 20 bar for 3 hours. This was dissolved in EA, washed with a saturated aqueous solution of 1N HCl, dried over $Na_2SO_4$ and filtered, and the solvent was removed by distillation under reduced pressure. Compound 21d was obtained by purifying by MPLC (C18 column, $R_f$=0.21, $H_2O$:MeOH=7:3) in a yield of 36.1%.

$^1$H NMR (500 MHz, $CDCl_3$) d 7.79 (d, J=6.5 Hz, 2H), 7.36 (d, J=6.4 Hz, 2H), 7.08 (s, 1H), 6.41 (s, 1H), 6.46 (s, 2H), 3.08 (s, 3H), 3.06-3.03 (m, 1H), 0.98 (d, J=5.3 Hz, 6H).

27. N-(4-(ethylcarbamoyl)benzyl)-2,4-dihydroxy-5-isopropyl-n-methylbenzamide (21e)

Compound 20b (0.22 g, 0.64 mmol), 70% ethylamine in d-water (0.08 ME, 0.97 mmol), HOBt (0.09 g, 0.64 m EDC (025 g, 1.29 mmol) and DIPEA (0.12 mL, 0.64 mmol) were dissolved in DMF, and microwave reaction was performed at 120° C. and 20 bar for 3 hours. It was dissolved in EA, washed with a saturated aqueous solution of 1N HCl, dried over $Na_2SO_4$ and filtered, and the solvent was removed by distillation under reduced pressure. Compound 21e was obtained by purifying by MPLC (C18 column, $R_f$=0.21, $H_2O$:MeOH=7:3) in a yield of 24.3%.

$^1$H NMR (500 MHz, $CDCl_3$) d 7.78 (d, J=6.6 Hz, 2H), 7.33 (d, J=6.6 Hz, 2H), 7.05 (s, 1H), 6.43 (s, 1H), 4.73 (s, 2H), 3.52-3.47 (m, 2H), 3.07-3.05 (m, 1H), 3.05 (s, 3H), 1.27-1.23 (m, 3H), 0.98 (d, J=5.4 Hz, 6H).

28. 2,4-dihydroxy-5-isopropyl-n-methyl-n-(4-(propylcarbamoyl)benzyl) benzamide (21f)

Compound 20b (0.22 g, 0.64 mmol), propylamine (0.08 mL, 0.96 mmol), HOBt (0.09 g, 0.64 mmol), EDC (0.25 g, 1.28 mmol)), DIPEA (0.11 mL, 0.64 mmol) were dissolved in DMF and microwave reaction was performed at 120° C. and 20 bar for 3 hours. It was dissolved in EA, washed with a saturated aqueous solution of 1N HCl, dried over $Na_2SO_4$, filtered, and then the solvent was removed by distillation under reduced pressure. Compound 21f was obtained by purifying by MPLC (C18 column, $R_f$=0.21, $H_2O$:MeOH=7:3) in a yield of 22.3%.

$^1$H NMR (500 MHz, $CDCl_3$) d 7.76 (d, J=6.6 Hz, 2H), 7.29 (d, J=6.6 Hz, 2H), 7.02 (s, 1H), 6.43 (s, 1H), 4.70 (s, 2H), 3.41-3.37 (m, 2H), 3.07-3.05 (m, 1H), 3.02 (s, 3H), 1.63 (s, 2H), 0.97-0.92 (m, 9H).

29. N-benzyl-2,4-dihydroxy-5-isopropyl-n-methyl-benzamide (21 g)

2,4-Dihydroxy-5-isopropylbenzoic acid (0.33 g, 1.70 mmol), N-methylaniline (0.33 g, 2.54 mmol), EDC (0.65 g, 3.30 mmol) and DIPEA (0.30 mL, 1.70 mmol) were dissolved in DMF and microwave reaction was performed at 120° C. and 20 bar for 3 hours. It was dissolved in EA, washed with a saturated aqueous solution of 1N HCl, dried with $Na_2SO_4$, filtered, and then the solvent was removed by distillation under reduced pressure. After purification using a mixed solvent of EA:hexane=1:4 ($R_f$=0.18), Compound 21g was obtained in a yield of 15.5%.

$^1$H NMR (500 MHz, $CDCl_3$)δ10.5(s,1H), 7.42-7.39(m, 2H), 7.34-7.29(m,3H), 6.38(s,1H), 5.34(s,1H), 4.74(s,2H), 3.09(s,3H), 3.06-2.95(m,1H), 0.96(d, J=5.4 Hz, 6H).

EXAMPLE 4

Evaluation of Biological Activity of Benzamide Compounds

1. Evaluation of Binding Ability to HSP90

Fluorescence polarization assay was performed to confirm the binding ability to the compound synthesized with HSP90 according the concentration. 1 M dithiothreitol (DTT), 10 mg/m: BGG (bovine gamma globulin) were added to hexafluorobenzene (HFB) buffer (20 mM HEPES pH 7.3, 50 mM KCl, 5 mM $MgCl_2$, 20 mM $Na_2MoO_4$, 0.01% $NP_4O$, $3^{rd}$ distilled water) and mixed. Then, 100 nM gambogic acid (GA)-FITC (Fluorescein isothiocyanate) was added and reacted at room temperature for 10 minutes. Each 100 μL of the mixture was dispensed into the control wells of a 96-well plate, 2 μL of HSP90α was added to the remaining mixture, and each 100 μL of the other wells was dispensed. Each 98 μL was dispensed into the wells to which the compound was to be treated, and then each 2 μL was added at 5 mM, 2.5 mM, 500 μM, 50 μM, 25 μM, 5 μM, 500 nM or 50 nM for each concentration. After 1, 4, 6, or 18 hours of reaction, fluorescence polarization was measured at 495/530 nm by a plate reader. The binding ability of the compound to HSP90 was expressed as mP (millipolarization unit=1000 mP unit). The results are shown in Table 3 below.

2. Measurement of Cell Viability

To confirm the cell viability according to the concentration of the compound synthesized in H1975 cells (ATCC) resistant to Gefitinib, MTS [3-(4,5-dimethylthiazol-2-yl)-5-(3-methylpiperidin-3-y)-carboxymethoxyphenyl)-2-(4-sulfophenyl)-2H-terazolium, inner salt] analysis was performed. When the cells were cultured so as to occupy 80% of the bottom of the culture dish, the cells were detached and diluted with RPMI 1640 medium to a concentration of $1.5 \times 10^3$ cells/well. Each 100 μL of the suspension was added to each well of a 96-well plate and cultured for 14 hours. Then, the medium was changed to the culture solution treated with compound of each concentration each concentration (1a-g: 0, 1, 5, 10, 30, 50 or 100 μM, 14a-I, 16a, b, 21a-f: 0, 0.01, 0.1, 1, 5, 10, 30, 50, 70 or 100 μM, and cultured for 3 days. Each 20 μL of the NITS solution was dispensed into each well and reacted for 1 hour at 37° C. in an incubator supplied with 5% $CO_2$. The absorbance was measured at 490/690 nm for 1 hour using a microplate reader, and the cell viability according to concentration was calculated as a percentage (%) and an $IC_{50}$ (μM). The results are shown in Table 3 below

[Chemical Formula 2]

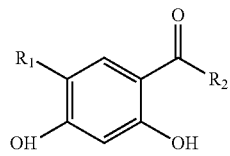

TABLE 3

| compound | $R_1$ | $R_2$ | HSP90 FP ($IC_{50}$; nM) | H1975 ($EC_{50}$; μM) |
|---|---|---|---|---|
| 14a | Cl | 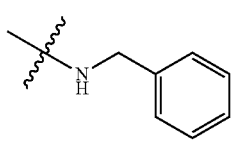 [SMILES: *NCc1ccccc1] | 6683 | 86.2 |
| 14b | Cl | 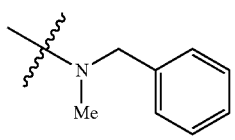 [SMILES: *N(C)Cc1ccccc1] | 413 | 35.5 |

TABLE 3-continued

| compound | R₁ | R₂ | HSP90 FP) (IC$_{50}$; nM) | H1975 (EC$_{50}$; μM) |
|---|---|---|---|---|
| 14c | Cl | N(Me)CH₂-(4-OMe-C₆H₄) | 135 | 16.7 |
| 14d | Cl | N(Me)CH₂-(3,4-diOMe-C₆H₃) | 362 | 33.4 |
| 14e | Cl | N(Me)CH₂-(3,4-methylenedioxyphenyl) | 585 | 103 |
| 14f | Cl | N(Me)CH₂-(3,4,5-triOMe-C₆H₂) | 1461 | 73.1 |
| 14g | Cl | N(Me)CH₂-(2-Cl-3,4,5-triOMe-C₆H) | 429 | 33.8 |
| 14h | Cl | N(Me)CH₂-(2-Br-3,4,5-triOMe-C₆H) | 528 | 34.3 |
| 14i | Cl | N(Me)CH₂-(2-Me-C₆H₄) | 995 | 47.5 |
| 16a | Cl | N(Me)CH₂-(3-Me-C₆H₄) | 830 | 49.3 |
| 16b | Cl | N(Me)CH₂-(4-Me-C₆H₄) | 558 | 34.3 |

TABLE 3-continued

| compound | R₁ | R₂ | HSP90 FP) (IC$_{50}$; nM) | H1975 (EC$_{50}$; μM) |
|---|---|---|---|---|
| 21a | Cl | 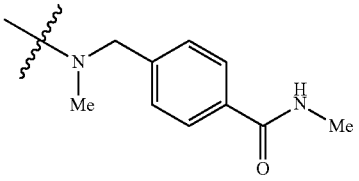 [SMILES: *N(C)Cc1ccc(C(=O)NC)cc1] | 496.0 | 34.8 |
| 21b | Cl | 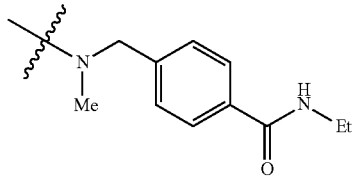 [SMILES: *N(C)Cc1ccc(C(=O)NCC)cc1] | 611.5 | 21.7 |
| 21c | Cl | 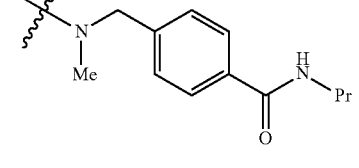 | 454.0 | 20.8 |
| 21d | isopropyl | 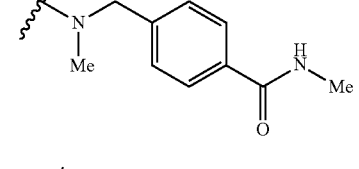 | 11.4 | 0.83 |
| 21e | Isopropyl | 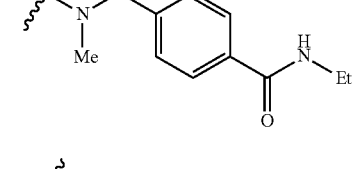 | 6.5 | 0.46 |
| 21f | isopropyl | 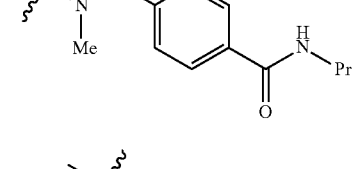 | 5.3 | 0.42 |
| 21g | isopropyl |  | 33 | 4.1 |

As a result of measuring the binding ability between the benzamide compounds 14a to 14i, 16a, 16b and 21a to 21f and HSP90 according to the present invention shown in the Table 3, the remaining compounds other than 14a and 14f exhibited a high binding ability at the nanomol level concentration. Among them, Compound 21f showed the best binding ability with IC$_{50}$ of 5.3 nM.

Furthermore, as a result of the cell viability of the compound was measured in H1975 cells shown in the Table 3, it was confirmed that cell proliferation was inhibited by all benzamide compounds in a time-dependent manner. In particular, Compound 21f exhibited good efficacy with an EC$_{50}$ of 420 nM.

3. Analysis of Protein Expression

Compound 21f having good efficacy was selected and HSP90 client protein proliferation effect in the same cell line was confirmed, in which the HSP90 client proteins were Her2 (human EGFR-related 2), EGFR (epidermal growth factor receptor), Met and c-Raf were used.

H1975 cells resistant to Gefitinib were cultured in a medium supplemented with 10% fetal bovine serum (FBS) for 24 hours, and the cells were detached, harvested and diluted with a RPMI 1640 medium so as to be $5 \times 10^5$ cells/well. Each 5 mL of the suspension was added to 6 mm culture dish and cultured for 24 hours. Then, the medium was changed to the culture solution treated with each compound of concentration (21f 0, 0.05, 0.1, 0.5 or 1 µM, GA: 1 µM), and cultured for 24 hours. After culture, the cells were harvested and centrifuged at 1300 rpm for 5 minutes at 4° C., and the supernatant was removed. The pellet was washed with phosphate buffered saline, centrifuged once again under the same conditions, and the supernatant was removed. Lysis buffer was added to the remaining pellet and lysed by vortexing at 5 minute intervals for 30 minutes. The supernatant was separated by centrifugation at 16000 rcf for 4 minutes at 4° C., and proteins were quantified using BCA (bovine serum albumin) kit. SDS-PAGE (sodium dodecylsulfate-polyacrylamide gel electrophoresis) was performed using 10, 12% running gel and 4% stacking gel (10 mA per gel). The separated proteins were transferred to an immunoblot PVDF, membrane (polyvinylidene fluoride membrane) at 100 V for 75 minutes. The membranes were blocked with 5% skim milk solution for 2 hours and then added a primary antibody diluted in the ratio of 1:750-1,000 in 0.1% tween-20 solution and reacted at 4° C. for 12 hours. After washing three times with TBS-T (Tris-buffered saline and Tween 20 containing Tween 20) and detected with an image analyzer using ECL (enhanced chemiluminescence) solution.

Figure 5:
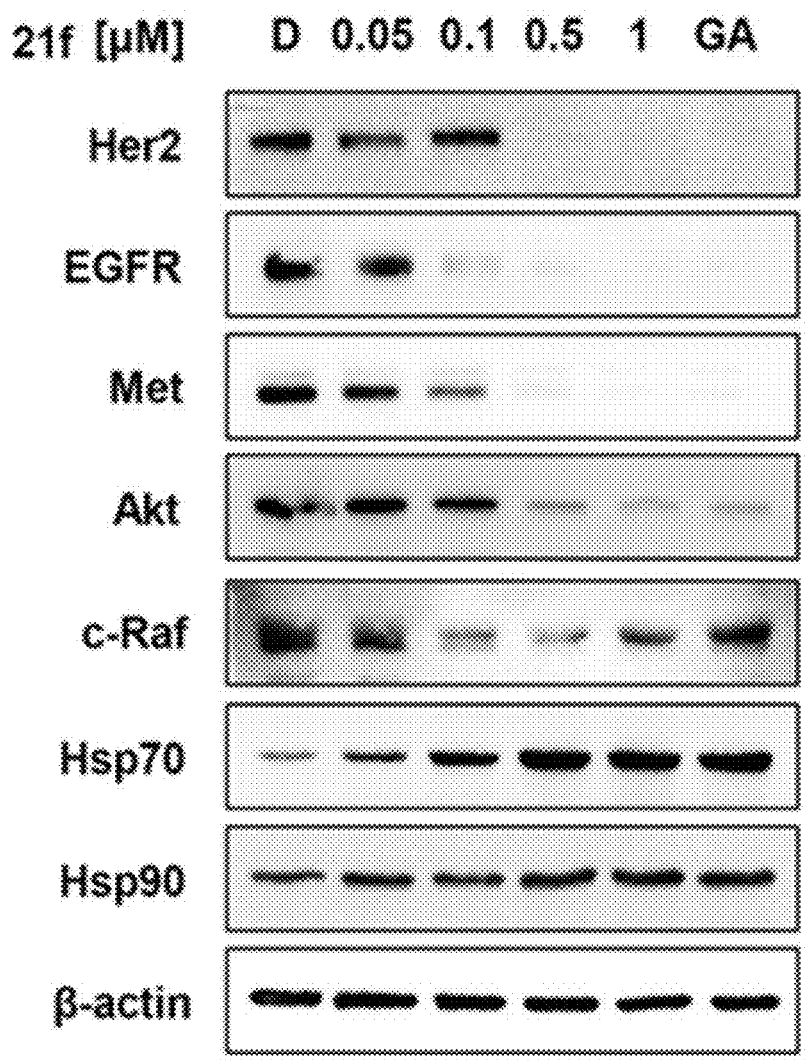
FIG. 5 is a graph showing the HSP90 inhibitory effect of the 2,4-dihydroxy-5-isopropy-methyl-N-(4-(propylcarbamoyl)benzyl) benzamide of compounds according to the present invention.

As a result of FIG. 5, it was confirmed that the proliferation of the HSP90 client protein was inhibited in a concentration-dependent manner by treatment with Compound 21f. The expression was significantly decreased at 0.5 µM for Her2, Met, and Akt, and 0.1 µM for EGFR. In addition, expression of HSP70 was also increased at 0.5 µM.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A compound of Chemical Formula 2 or a pharmaceutically acceptable salt thereof:

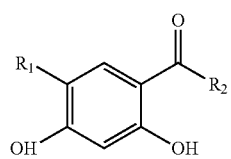

Chemical Formula 2 wherein $R_1$ is isopropyl, and
$R_2$ is

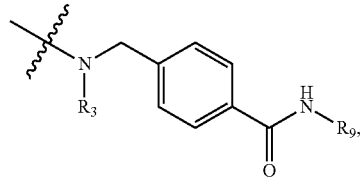

$R_3$ is methyl, and
$R_9$ is methyl, ethyl, or propyl.

2. A method of treating heat shock protein 90 (HSP90)-mediated disease in a subject in need thereof, comprising administering an effective amount of a pharmaceutical composition comprising a compound of following Chemical Formula 2 or a pharmaceutically acceptable salt thereof, as an active ingredient:

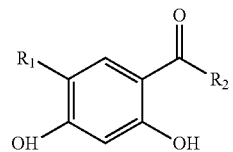

Chemical Formula 2 wherein $R_1$ is isopropyl, and
$R_2$ is

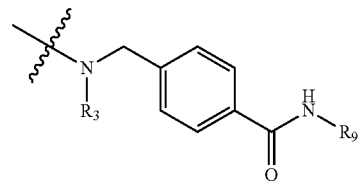

$R_3$ is methyl, and
$R_9$ is methyl, ethyl, or propyl,
to the subject, wherein the heat shock protein 90 (HSP90)-mediated disease is selected from the group consisting of cancer disease, degenerative neurological disease, and viral infection.

3. The method of claim 2, the cancer disease is any one selected from the group consisting of non-small cell lung cancer, breast cancer, ovarian cancer, uterine cancer, pancreatic cancer, lung cancer, gastric cancer, liver cancer, colon cancer, skin cancer, head or neck cancer, brain cancer, laryngeal cancer, prostate cancer, bladder cancer, esophageal cancer, thyroid cancer, kidney cancer, rectal cancer, acute myelogenous leukemia, chronic myelogenous leukemia, acute lymphoblastic leukemia, chronic lymphocytic leukemia, and blood cancer.

4. The method of claim 2, wherein the degenerative neurological disease is any one selected from the group consisting of stroke, paralysis, memory loss, memory impairment, dementia, forgetfulness, Parkinson's disease, Alzheimer's disease, Pick's disease, Creutzfeld-Kacob disease, Huntington's disease, and amyotrophic lateral sclerosis.

* * * * *